US011299517B2

United States Patent
Yu et al.

(10) Patent No.: US 11,299,517 B2
(45) Date of Patent: Apr. 12, 2022

(54) RECOMBINANT VACCINE AGAINST MAREK'S DISEASE AND NEWCASTLE DISEASE

(71) Applicant: The United States of America, as represented by the Secretary of Agriculture, Washington, DC (US)

(72) Inventors: Qingzhong Yu, Athens, GA (US); Stephen J. Spatz, Bogart, GA (US); John R. Dunn, East Lansing, GA (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 36 days.

(21) Appl. No.: 16/848,880

(22) Filed: Apr. 15, 2020

(65) Prior Publication Data
US 2021/0324016 A1  Oct. 21, 2021

(51) Int. Cl.
| | |
|---|---|
| *C07K 14/125* | (2006.01) |
| *C07K 14/055* | (2006.01) |
| *C12N 7/00* | (2006.01) |
| *A61K 35/76* | (2015.01) |
| *A61K 39/17* | (2006.01) |
| *A61K 38/00* | (2006.01) |

(52) U.S. Cl.
CPC .......... *C07K 14/125* (2013.01); *C07K 14/055* (2013.01); *C12N 7/00* (2013.01); *A61K 38/00* (2013.01)

(58) Field of Classification Search
None
See application file for complete search history.

(56) References Cited

PUBLICATIONS

Huang et al. A Recombinant Newcastle Disease Virus (NDV) Expressing VP2 Protein of Infectious Bursal Disease Virus (IBDV) Protects against NDV and IBDV. Journal of Virology, Sep. 2004, vol. 78, p. 10054-10063.*
Huang et al. Recombinant Newcastle Disease Virus as a Vaccine Vector. Poultry Science, 2003, 82:899-906.*
Ross L., Recombinant vaccines against Marek's disease. Avian Pathology (1998) 27, S65-S73.*
YP_001033956.1. envelope glycoprotein B [Gallid alphaherpesvirus 2], Dated Aug. 13, 2018.*

* cited by examiner

*Primary Examiner* — Nianxiang Zou
(74) *Attorney, Agent, or Firm* — John D. Fado; Mark D. McNemar

(57) ABSTRACT

Provided herein are immunogenic compositions containing recombinant viruses capable of inducing protection in poultry against both Marek's disease virus (MDV) and Newcastle disease virus (NDV). Such viruses incorporate nucleic acids for expressing at least one MDV antigen, such as glycoprotein B, and antigenic portions thereof, in a recombinant NDV genome.

14 Claims, 3 Drawing Sheets
(3 of 3 Drawing Sheet(s) Filed in Color)
Specification includes a Sequence Listing.

RECOMBINANT VACCINE AGAINST MAREK'S DISEASE AND NEWCASTLE DISEASE

BACKGROUND OF THE INVENTION

Field of Invention

The subject matter disclosed herein provides immunogenic compositions containing recombinant vaccines against Marek's disease and Newcastle disease. These vaccine compositions contain recombinant viruses capable of inducing protection in recipients, such as poultry, against both Marek's disease virus (MDV) and Newcastle disease virus (NDV). Such viruses incorporate nucleic acids for expressing at least one MDV antigen (e.g., glycoprotein B) in a recombinant NDV genome.

Background

Newcastle disease (ND), caused by infection of Avian orthoavulavirus 1, commonly known as Newcastle disease virus (NDV, used hereafter), is one of the most serious infectious diseases in poultry (Miller and Koch, 2013). All known strains of NDV are of a single serotype, but three different pathotypes have been described: velogenic (highly virulent), mesogenic (moderately virulent), and lentogenic (low virulence) viruses. Velogenic strains can cause severe disease, characterized by extensive lesions and high mortality in both the laboratory and field, and such outbreaks require reporting to the World Organization for Animal Health (OIE) by member nations.

NDV contains a single-strand, non-segmented, negative-sense RNA genome that consists of six genes flanked by a 3' Leader and 5' Trailer in the order 3'-nucleocapsid protein (NP)-phosphoprotein (P)-matrix protein (M)-fusion protein (F)-hemagglutinin-neuraminidase (HN)-large polymerase (L)-5' (de Leeuw and Peeters, 1999; Peeters et al., 1999; Samal, 2011). Unlike positive-stranded RNA viruses, the naked genomic RNA of NDV is not infectious. It must be encapsidated with the NP protein and associated with the P and L proteins, forming a ribonucleocapsid, to act as an template for RNA transcription and replication (Peeters et al., 1999).

Vaccination combined with strict biosecurity practices have been recommended for controlling NDV outbreaks for over 60 years (Dimitrov et al, Vet. Microbiol., (2017) 206:-126-36). The NDV LaSota strain, a naturally-occurring low virulence NDV strain, has been routinely used as a live vaccine throughout the world for more than fifty years to prevent ND (Goldhaft, T., Avian Dis. (1980) 24:297-301). This vaccine strain induces strong immunity both locally and systemically and can be readily administered through drinking water supplies or by directly spraying the birds. The LaSota vaccine has been proven to be safe and stable, and there are no reports of virulence reversion or recombination for this vaccine strain to generate new virulent strains.

Marek's disease (MD) is a highly contagious immunosuppressive and neoplastic disease of chickens caused by a cell-associated herpesvirus, gallid alphaherpesvirus type 2 (GaHV-2), commonly known as Marek's disease virus (MDV) (Osterrieder et al, Nat. Rev. Microbiol., (2006) 4:283-94). Some characteristics of MD include T-cell lymphomas, infiltration of nerves and organs by lymphocytes, and immunosuppression (Boodhoo et al, Vet. Res., (2016) 47:119).

In the commercial poultry industry, Marek's disease manifests itself through increased condemnation rates for skin leukosis, visceral lymphomas, and secondary adventitious infections. The disease cannot be treated post-infection, but vaccination in ovo or at day of hatch can prevent and minimize the impact of the disease. Vaccines have been paramount in curtailing losses due to MD (Schat, K., Avian Dis., (2016) 60:715-724). The first vaccine (circa 1969) was a modified live strain HPRS-16/att that was attenuated by in vitro serial passage of a virulent strain (Churchill et al, J. Gen. Virol., (2016) 4:557-64; Churchill et al, Nature, (1969) 221:744-7). However, due to its poor replication rates in chicken, it was replaced with an antigenically related virus, turkey herpesvirus (HVT). Over the last half-century of high-density commercial poultry production, Marek's disease viruses have evolved to higher degrees of virulence as reflected by increased levels of lymphomas and paralysis (Witter, R, Avian Dis., (1983) 27:113-32), and newer vaccines like SB-1 and 301B/1 (Schat et al, Avian Pathol., (1982) 11:593-605) were introduced periodically to control the disease (Witter et al, Avian Dis., (1987) 31:829-40).

In the US, MD is controlled through the near-ubiquitous application of live infected cellular preparations of MD vaccines, i.e., Rispens, HVT, SB-1, or combination of these vaccine viruses (Rispens et al, Avian Dis., (1972) 16:126-38; Witter et al, Poultry Sci., (1985) 64:2280-6). These vaccines consist of infected chicken embryo fibroblasts (CEFs) and not "cell-free" viruses. They can only be used in modern industrialized countries because they are unstable at temperatures greater than −80° C. In countries where liquid nitrogen is not practical or available, it is impossible to maintain the cold chain, and thus, these countries cannot vaccinate against Marek's disease and thereby suffer tremendous poultry losses due to condemnation. Even in modern countries, vaccine failure often occurs due to incorrect thawing of the vaccine ampoules or extended handling times. Therefore, there is a pressing need to develop a safe and efficacious vaccine that can be produced, transported, and administered at ambient temperatures.

To overcome these problems associated with the MDV vaccines, we have developed a novel, Newcastle disease virus (NDV) vaccine strain-based recombinant virus expressing glycoprotein B (gB) of MDV as a dual vaccine against MD and Newcastle disease. Glycoprotein B is the major antigen of MDV and is the fusogen necessary for penetrating susceptible cells (Schat & Nair, "Marek's Disease," p. 515-52, in Swayne D E, Glisson J R, McDougald L R, Nolan L K, Suarez D L, Nair V (ed), Diseases of Poultry, 13th ed. Wiley-Blackwell Publishing, Ames, Iowa, USA). As reported herein, we have generated an NDV LaSota strain-based recombinant virus expressing the gB of MDV as a dual vaccine candidate using reverse genetics technology. Biological assessments and evaluations of the vaccine in chickens showed that the recombinant virus expressing the MDV gB protein is a safe and efficacious dual vaccine candidate against MDV and NDV challenges.

SUMMARY OF THE INVENTION

The present disclosure provides a composition comprising a nucleic acid at least 95% identical to SEQ ID NO:3. In some embodiments, the nucleic acid is at least 99% identical to SEQ ID NO:3. Also provided herein are vectors containing this nucleic acid.

Also provided herein is a recombinant Newcastle disease virus (NDV) comprising a synthetic polypeptide having an amino acid sequence at least 95% identical to SEQ ID NO:2.

In some embodiments, the synthetic polypeptide has at least 98% identical to SEQ ID NO:2. In specific embodiments, such viruses are combined with a pharmaceutically or veterinarily acceptable carrier. In some embodiments, the NDV strain is LaSota.

The present disclosure also provides a method of eliciting an immune response against Marek's disease virus (MDV) and Newcastle disease virus (NDV) in a subject, by administering a composition comprising a recombinant NDV expressing a synthetic polypeptide having an amino acid sequence at least 95% identical to SEQ ID NO:2 to the subject. In some embodiments, the synthetic polypeptide has an amino acid sequence at lease 98% identical to SEQ ID NO:2. In particular embodiments, the synthetic polypeptide is identical to SEQ ID NO:2. In some embodiments, the recombinant NDV has a nucleic acid with at least 99% identity to SEQ ID NO:3. In specific embodiments, the recombinant NDV is identical to SEQ ID NO: 3. In preferred embodiments, the subject is poultry, such as chicken.

INCORPORATION BY REFERENCE

All publications, patents and patent applications mentioned in this specification are herein incorporated by reference to the same extent as if each publication, patent or patent application was specifically and individually indicated to be incorporated by reference.

BRIEF DESCRIPTION OF THE DRAWINGS

The patent application file contains at least one drawing executed in color. Copies of this patent or patent application publication with color drawing(s) will be provided by the Office upon request and payment of the necessary fee.

The novel features of the invention are set forth with particularity in the claims. Features and advantages of the present invention are referred to in the following detailed description and the accompanying drawings of which:

FIG. 1 provides a schematic representation of the construction of an exemplary recombinant NDV containing the gB gene of MDV (rLS/MDV-gB). The gB gene of MDV was optimized for codon usage for chickens. The ORF of the gB gene and the vector (pLS-GFP), containing the gene encoding green fluorescent protein (GFP), were amplified by PCR using gB- and vector-specific primers. The amplified gB ORF was cloned as an independent transcription unit into the pLS-GFP vector to replace the GFP gene. The direction of the T7 promoter is indicated by the bold arrow. HDVRz and T71 represent the site of a hepatitis delta virus ribozyme and T7 terminator sequences, respectively.

FIG. 2 provides graphic representation of results from growth kinetics analyses of the recombinant NDV expressing the gB gene of MDV (rLS/MDV-gB) compared with parental rLaSota and rLS/GFP viruses. DF-1 cells were infected with each virus separately at a multiplicity of infection (MOI) of 0.01. Viral titers were determined by the 50% tissue culture infective dose ($TCID_{50}$) assay for each time point in triplicates. The mean titer of each time point is expressed in $Log_{10}$ $TCID_{50}$/mL.

DETAILED DESCRIPTION OF THE INVENTION

Figure 3:
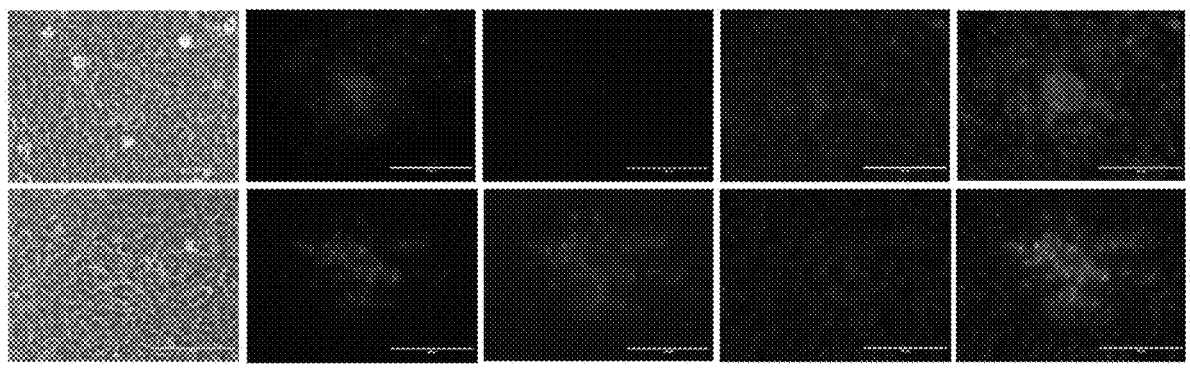
FIG. 3 provides photomicrographs demonstrating the detection of MDV-gB and NDV HN protein expression by immunofluorescence assay (IFA). DF-1 cells were infected with rLaSota (top row) and rLS/MDV-gB (bottom row). At 24-hours post-infection, cells were fixed and stained with a mixture of chicken anti-MDV serum (Md11) and mouse anti-NDV HN monoclonal antibody, followed by a mixture of FITC-labeled goat anti-chicken IgG (third column) and ALEXA FLUOR 568-labeled goat anti-mouse IgG (second column). Infected cells were examined for cytopathic effect without fluorescence (first column) and were also stained with DAPI (fourth column). Photomicrographs are shown at 400× magnification. Green, red, and blue fluorescent images taken from the same field of virus-infected cells were merged into single images (fifth column). Bars represent 100 µm.

Marek's disease (MD) is a highly contagious viral neoplastic disease of chickens caused by Marek's disease virus (MDV), resulting in significant economic losses to the poultry industry worldwide. The commonly used live and vectored MDV vaccines can prevent tumor formation in vaccinated chickens, but do not elicit sterilizing immunity. Furthermore, they are expensive to produce, store and ship. Except for the lyophilized serotype-3 HVT vaccine, liquid nitrogen is required for storage, shipment, and farm-side administration due to the instability of live vaccine-infected cells. To overcome these shortcomings of current vaccines, we developed a recombinant Newcastle disease virus (NDV) expressing the MDV glycoprotein B (gB) as a dual vaccine. The synthetic gB gene of MDV was optimized for chicken codon usage and cloned into the NDV LaSota vaccine infectious clone. The resulting recombinant virus, named rLS/MDV-gB, was rescued using reverse genetics technology. The biological assessments of the rLS/MDV-gB virus showed that it was slightly attenuated in vivo, yet retained similar growth kinetics and comparable in vitro virus titers relative to the parental LaSota virus. An indirect immunofluorescence assay was used to detect the expression of MDV glycoprotein B in recombinant virus-infected DF-1 cells. Vaccination of specific-pathogen-free leghorn chickens with rLS/MDV-gB conferred significant protection against virulent MDV challenge and complete protection against the velogenic NDV challenge. These results demonstrated that the rLS/MDV-gB is a safe, stable, inexpensive, and effective bivalent vaccine.

This dual vaccine against Marek's disease and Newcastle disease can be readily administered through any method known in the art, such as via drinking water, or by direct spray (Meulemans, G., "Control By Vaccination," in Alexander D J (ed), Newcastle Disease. Kluwer Academic Publishers, Boston, Mass.), thus eliminating the cold chain requirement of the most prevalent commercial MDV vaccines. The exemplary NDV vector utilized herein is based on a naturally occurring low virulence NDV strain (LaSota) that has been used as a live vaccine (Ayala et al, PLoS One, (2016) 11:e0162484; Dimitrov et al, supra; Goldhaft, T., supra). This vaccine strain induces strong immunity, both mucosal and systemic, and has been proven to be safe and stable with no reports of virulence reversion or recombination with field strains. The recombinant NDV vaccine reported here can be lyophilized, stored, and transported at ambient temperatures and readily administered to large populations of chickens through drinking water supplies or by direct spray at a low cost.

Preferred embodiments of the present invention are shown and described herein. It will be obvious to those skilled in the art that such embodiments are provided by way of example only. Numerous variations, changes, and substitutions will occur to those skilled in the art without departing from the invention. Various alternatives to the embodiments of the invention described herein may be employed in practicing the invention. It is intended that the included claims define the scope of the invention and that methods and structures within the scope of these claims and their equivalents are covered thereby.

Technical and scientific terms used herein have the meanings commonly understood by one of ordinary skill in the art to which the instant invention pertains, unless otherwise defined. Reference is made herein to various materials and methodologies known to those of skill in the art. Standard reference works setting forth the general principles of recombinant DNA technology include Sambrook et al., "Molecular Cloning: A Laboratory Manual", 2d ed., Cold Spring Harbor Laboratory Press, Plainview, N.Y., 1989; Kaufman et al., eds., "Handbook of Molecular and Cellular Methods in Biology and Medicine", CRC Press, Boca Raton, 1995; and McPherson, ed., "Directed Mutagenesis: A Practical Approach", IRL Press, Oxford, 1991. Standard reference literature teaching general methodologies and principles of NDV reverse genetics and the development of recombinant vaccines include: Cardenas-Garcia & Afonso, Methods Mol. Biol., (2017), 1602:141-58; Kim & Samal, Curr. Protocols Mol. Biol., (2018) 48:18.5.1-18.5.12).

Any suitable materials and/or methods known to those of skill can be utilized in carrying out the instant invention. Materials and/or methods for practicing the instant invention are described. Materials, reagents and the like to which reference is made in the following description and examples are obtainable from commercial sources, unless otherwise noted.

As used in the specification and claims, use of the singular "a", "an", and "the" include plural references unless the context clearly dictates otherwise.

The term "about" is defined as plus or minus ten percent of a recited value. For example, about 1.0 g means 0.9 g to 1.1 g and all values within that range, whether specifically stated or not.

The terms "consisting essentially of" and "consists essentially of" have the meaning ascribed to them in U.S. Patent law, namely, they allow for elements not explicitly recited, but exclude elements that are found in the prior art or that affect a basic or novel characteristic of the invention.

The term "gB" or "glycoprotein B" refers herein to the glycoprotein B protein from Marek's Disease Virus (SEQ ID NO: 2). In context, the term can also refer to an open reading frame encoding this protein, such as the sequence of SEQ ID NO: 1 (codon optimized for expression in Gallus gallus), positions 3310-5907 of SEQ ID NO:3 and complementary sequences. These terms also refer to modified versions of these SEQ ID NOs, such as those comprising regulatory nucleic acids, or proteins (and the nucleic acids encoding them) containing additional moieties allowing for purification (e.g., His tag), or immunogenicity-enhancement. For example, SEQ ID NO: 3 comprises a Kozak (translation enhancement) sequence at position 3303-3309. Where indicated, these terms can also include antigenic sub-portions of the provided protein sequence.

As used herein, the term "poultry" refers to one bird, or a group of birds, of any type of domesticated birds typically kept for egg and/or meat production. For example, poultry includes chickens, ducks, turkeys, geese, bantams, quail, pheasant, pigeons, or the like, preferably commercially important poultry such as chickens, ducks, geese and turkeys.

The terms "isolated", "purified", or "biologically pure" as used herein, refer to material that is substantially, or essentially, free from components that normally accompany the referenced material in its native state.

The term "codon optimization" refers to the process of optimally configuring the nucleic acid sequence encoding a protein or polypeptide for expression or translation in a selected host. In general, if a gene contains codons that are rarely used by the host, its expression level will not be maximal. This may be one of the limitations of heterologous protein expression and the development of DNA vaccines. Codon usage optimization typically involves altering the rare codons in the target gene so that they more closely reflect the codon usage of the host without modifying the amino acid sequence of the encoded protein (Gustafsson, C., Trends Biotechnol. 22, 346-353, 2004). The information usually used for the optimization process is therefore the DNA or protein sequence to be optimized and a codon usage table (reference set) of the host.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

Molecular Biological Methods

An isolated nucleic acid is a nucleic acid the structure of which is not identical to that of any naturally occurring nucleic acid. The term therefore covers, for example, (a) a DNA which has the sequence of part of a naturally occurring genomic DNA/RNA molecule but is not flanked by both of the coding or noncoding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), a chemically synthesized fragment, or a restriction fragment; and (d) a recombinant nucleotide sequence that is part of a hybrid gene, i.e., a gene encoding a fusion protein. Specifically excluded from this definition are nucleic acids present in mixtures of (i) DNA molecules, (ii) transformed or transfected cells, and (iii) cell clones, e.g., as these occur in a DNA library such as a cDNA or genomic DNA library.

The term recombinant nucleic acids refers to polynucleotides which are made by the combination of two otherwise separated segments of sequence accomplished by the artificial manipulation of isolated segments of polynucleotides by genetic engineering techniques or by chemical synthesis. In so doing one may join polynucleotide segments of desired functions to generate a desired combination of functions.

In practicing some embodiments of the invention disclosed herein, it can be useful to modify the genomic sequence of a recombinant virus producing glycoprotein B. Such modification can involve deletion of all or a portion of a target gene, including but not limited to the open reading frame of a target locus, transcriptional regulators such as promoters of a target locus, and any other regulatory nucleic acid sequences positioned 5' or 3' from the open reading frame. Such deletional mutations can be achieved using any technique known to those of skill in the art. Mutational, insertional, and deletional variants of the disclosed nucleotide sequences and genes can be readily prepared by methods which are well known to those skilled in the art. Thus, while the present disclosure provides an exemplary insertional recombinant virus (SEQ ID NO: 3), the placement of the gB coding sequence is not limited to this example within a Newcastle disease virus genome. It is well within the skill of a person trained in this art to make mutational, insertional, and deletional mutations which are equivalent in function to the specific ones disclosed herein.

Where a recombinant nucleic acid is intended for expression, cloning, or replication of a particular sequence, DNA constructs prepared for introduction into a prokaryotic or eukaryotic host will typically comprise a replication system (i.e. vector) recognized by the host, including the intended DNA fragment encoding a desired polypeptide, and can also include transcription and translational initiation regulatory sequences operably linked to the polypeptide-encoding segment. Expression systems (expression vectors) can include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences.

Nucleic acids and proteins of the present invention can also encompass sequences with high identity to the specifically disclosed sequences. Identity can be 50%-100%. In some instances, such identity is greater than 80%, greater than 85%, greater than 90%, or greater than 95%. In other embodiments, such identity is 90%, 91%, 92%, 93%, 94%, 95%, 96%, 97%, 98%, 99%, 99.1%, 99.2%, 99.3%, 99.4%, 99.5%, 99.6%, 99.7%, 99.71%, 99.72%, 99.73%, 99.74%, 99.75%, 99.76%, 99.77%, 99.78%, 99.79%, 99.8%, 99.81%, 99.82%, 99.83%, 99.84%, 99.85%, 99.86%, 99.87%, 99.88%, 99.89%, 99.9%, 99.91%, 99.92%, 99.93%, 99.94%, 99.95%, 99.96%, 99.97%, 99.98%, or 99.99%. The degree of homology or identity needed for any intended use of the sequence(s) is readily identified by one of skill in the art. As used herein percent sequence identity of two nucleic acids is determined using any algorithm known in the art, such as that disclosed by Karlin and Altschul (1990) Proc. Natl. Acad. Sci. USA 87:2264-2268, modified as in Karlin and Altschul (1993) Proc. Natl. Acad. Sci. USA 90:5873-5877. Such an algorithm is incorporated into the NBLAST and XBLAST programs of Altschul et al. (1990) J. Mol. Biol. 215:402-410. BLAST nucleotide searches are performed with the NBLAST program, score=100, wordlength=12, to obtain nucleotide sequences with the desired percent sequence identity. To obtain gapped alignments for comparison purposes, Gapped BLAST is used as described in Altschul et al. (1997) Nucl. Acids. Res. 25:3389-3402. When utilizing BLAST and Gapped BLAST programs, the default parameters of the respective programs (NBLAST and XBLAST) are used. See www.ncbi.nih.gov.

In one embodiment of the present invention, the vector utilized to express the MDV gB protein is a Newcastle Disease Virus (NDV) vector. Newcastle disease virus also designated as Avian orthoavulavirus 1 (family Paramyxoviridae, subfamily Avulavirinae, genus orthoavulavirus) is an avian pathogen in which naturally occurring strains exhibit a wide range of disease severity. NDV is particularly advantageous as a vaccine vector for veterinary use because the vector itself serves as a needed poultry vaccine. NDV strain pathotypes are asymptomatic enteric (e.g., Ulster 2C, Queensland V4), lentogenic (e.g., LaSota, $B_1B_1$, VG/GA), mesogenic (e.g., strain H, Mukteswar, Roakin, Beaudette C) or velogenic (e.g., Texas GB, NY parrot 70181, Italien, Milano, Herts 33/56, CA02). As NDV does not express all MDV proteins it is therefore compatible with a DIVA (differentiate infected from vaccinated animals) strategy.

Immunogenic Compositions

An immunogenic composition is defined herein as a biological agent (e.g., virus) which is capable of providing a protective response in an animal to which the immunogenic composition has been delivered and is incapable of causing severe disease. Administration of the immunogenic compositions result in increased immunity to a disease; the immunogenic compositions stimulate antibody production, cellular immunity, or both against the pathogen(s) causing the disease. Immunity is defined herein as the induction of a significantly higher level of protection in a population of recipients, such as poultry, against mortality and clinical symptoms after receipt of an immunogenic composition compared to an untreated group. In particular, the immunogenic composition(s) according to the invention can: (a) protect a large proportion of treated animals against the occurrence of clinical symptoms of the disease and mortality, or; (b) result in a significant decrease in clinical symptoms of the disease and mortality. In preferred embodiments, the vaccines or immunogenic compositions disclosed herein provide immunity against two diseases, specifically Marek's disease and Newcastle disease.

The immunogenic composition(s) of the invention herein, regardless of other components included, comprise a recombinant virus (e.g., NDV) expressing the gB gene of Marek's Disease Virus. In particular embodiments, the open reading frame for the gB gene is modified to reflect the codon usage of the target organism, for example Gallus gallus. In particular embodiments, the recombinant virus expressing the gB gene is a Newcastle Disease Virus.

The immunogenically effective amounts of immunogenic compositions disclosed herein can vary based upon multiple parameters. In general, however, effective amounts per dosage unit can be about $1 \times 10^{5-7}$ $EID_{50}$/bird, about $1 \times 10^{5-6}$ $EID_{50}$/bird, about $1 \times 10^{6-7}$ $EID_{50}$/bird, about $1 \times 10^{5}$ $EID_{50}$/bird, $1 \times 10^{6}$ $EID_{50}$/bird, or $1 \times 10^{7}$ $EID_{50}$/bird.

One, two, or more dosage units can be utilized in practicing the methodologies of the present invention. If two dosage units are selected, then vaccination at about day 1 post-hatch and again at about one week to two weeks of age is preferred. A dosage unit can readily be modified to fit a desired volume or mass by one of skill in the art. Regardless of the dosage unit parameters, immunogenic compositions and vaccines disclosed herein can be administered in an amount effective to produce an immune response to the presented viruses (e.g., NDV and MDV). An "immunogenically effective amount" or "effective amount" of an immunogenic composition as used herein, is an amount of the composition that provides sufficient levels of antigenic protein to produce a desired result, such as induction of, or increase in, production of antibody specific to the antigen, protection against coccidiosis, as evidenced by a reduction in gastrointestinal lesions, increased weight gain, and decreased oocyst shedding and other indicators of reduction in pathogenesis. Amounts of immunogenic compositions capable of inducing such effects are referred to as an effective amount, or immunogenically effective amount, of the immunogenic compositions.

Dosage levels of active ingredients (e.g., recombinant virus) in immunogenic compositions disclosed herein, can be varied by one of skill in the art to achieve a desired result in a subject or per application. As such, a selected dosage level can depend upon a variety of factors including, but not limited to, formulation, combination with other treatments, severity of a pre-existing condition, and the presence or absence of adjuvants. In preferred embodiments, a minimal dose of an immunogenic composition is administered. As used herein, the term "minimal dose" or "minimal effective dose" refers to a dose that demonstrates the absence of, or minimal presence of, toxicity to the recipient, but still results in producing a desired result (e.g., protective immunity). Minimal effective doses, or minimum immunizing doses, of the recombinant immunogenic compositions provided herein can include about $10^5$ to about $10^7$ $EID_{50}$ recombinant virus per bird. Determination of a minimal dose is well within the capabilities of one skilled in the art.

Efficacy of the vaccines of the present disclosure can be tested at least 2 weeks after the last immunization by challenging a recipient (e.g., poultry such as a chicken), with a virulent, heterologous or homologous strain of MDV, NDV or both. Animals can be observed daily following challenge for clinical signs and mortality. In addition, the groups of animals can be euthanized and evaluated for pathological findings. Relevant biological samples can be collected from recipients post challenge for virus detection. The presence or absence of viral antigens in tissues can be evaluated by any approach known in the art, including, but not limited to immunohistochemistry, viral isolation or titration, and nucleic acid detection. Blood samples may be collected post-challenge and may be analyzed for the presence of anti-MDV specific antibodies, anti-NDV specific antibodies, or both, as well as MDV- and/or NDV-reactive lymphocytes.

Formulations

In some instances, immunogenic compositions of the present invention also contain or comprise one or more adjuvants, which includes any material included in the immunogenic composition formulation that enhances an immune response in the recipient that is induced by the immunogenic composition. Such adjuvants include any adjuvant known in the art including, but not limited to, lipopolysaccharide (LPS) or toll-like receptor antagonists. Formulations of the present disclosure can also contain pharmaceutically or veterinarily acceptable carriers or vehicles or excipients. Such components are well known to the skilled artisan. For example, a pharmaceutically or veterinarily acceptable carrier or vehicle or excipient can be sterile water, a 0.9% NaCl (e.g., saline) solution or a phosphate buffer. Other pharmaceutically or veterinarily acceptable carrier or vehicle or excipients that can be used for methods of this invention include, but are not limited to, poly-(L-glutamate) or polyvinylpyrrolidone. The pharmaceutically or veterinarily acceptable carrier or vehicle or excipients may be any compound or combination of compounds facilitating the administration of the recombinant virus. Carriers, vehicles, or excipients can also facilitate preservation.

Administration Methodologies

The present disclosure provides compositions for introducing a recombinant immunogenic composition containing, at a minimum, a recombinant NDV virus expressing an MDV protein (e.g., glycoprotein B). Thus, the compositions provided herein can be utilized to induce immunity or resistance to both NDV and MDV in targets to which the composition is provided.

Recombinant viruses, immunogenic compositions and vaccines of the present invention can be administered to a recipient (e.g., poultry such as a turkey or chicken) via drinking water, in ovo, via sprays, aerosols, intranasally, or eye-dropping. Where a vaccine is administered in ovo, it can be administered 1-3 days before hatching. For other routes of administration, the recipient (e.g., chicken) can be 1 day old, 2 days old, 3 days old, 4 days old, 5 days old, 6 days old, 7 days old, 8 days old, 9 days old, 10 days old, 11 days old, 12 days old, 13 days old, 14 days old, 15 days old, 16 days old, 17 days old, 18 days old, 19 days old, 20 days old, or 21 days old.

In one embodiment of the invention, a "prime-boost" regimen can be employed, which is comprised of at least one primary administration and at least one booster administration using at least one common protein, polypeptide, antigen, epitope or immunogen. The immunological composition or vaccine used in primary administration can be different in nature from those used as a booster. However, it is noted that the same composition can be used as the primary administration and the boost. The primary administration, the boost administration, or both, can comprise one or more administrations. The various administrations can be carried out about 1 to about 6 weeks apart, or about 2 to about 4 weeks apart.

Application of an immunogenic composition of the present disclosure to a subject can result in the development of immunity to MDV and NDV, preferably development of an effective immune response that results in the decrease or removal of clinical symptoms. Application of the immunogenic compositions of the present invention can be performed before, during or after the development of Marek's disease, Newcastle disease, or both.

Having generally described this invention, the same will be better understood by reference to certain specific examples, which are included herein to further illustrate the invention and are not intended to limit the scope of the invention as defined by the claims.

EXAMPLES

Example 1

Construction and Propagation of an rLS/MDV-gB Virus.

Cell lines and viruses: HEp-2 (CCL-81; ATCC, Manassas, Va., USA) and DF-1 (CRL-12203; ATCC) cell lines were grown in Dulbecco's Modified Eagle Medium (DMEM, ThermoFisher Scientific, Carlsbad, Calif., USA) supplemented with 10% fetal bovine serum (FBS, ThermoFisher Scientific) and antibiotics (100 U/ml Penicillin, 100 µg/ml Streptomycin, 0.25 µg/ml Amphotericin B, ThermoFisher Scientific, Suwanee, Ga.) at 37° C. in 5% $CO_2$ atmosphere. DF-1 cells were maintained in DMEM supplemented with 10% allantoic fluid (AF) from 10-day-old specific-pathogen-free (SPF) chicken embryos for all subsequent infections unless otherwise indicated. The recombinant (rLaSota and rLS/GFP) viruses were generated as previously described (Hu et al, Vaccine, (2011), 29:8624-33; Zhao et al, J. Virol., (2014) 88:8397-406). The velogenic strain of NDV, California 2002 (NDV/CA02; game chicken/US(CA)/50212676/02), was obtained from the pathogen repository bank at the Southeast Poultry Research Laboratory (SEPRL, USDA-ARS, Athens, Ga., USA). A virulent MDV strain (JM/102W) was obtained from the pathogen repository bank at the Avian Disease and Oncology Laboratory (ADOL, USDA-ARS, East Lansing, Mich., USA). A modified vaccinia Ankara/T7 recombinant virus (MVA/T7) used during virus rescue to provide the bacteriophage T7 RNA polymerase was a kind gift from B. Moss, National Institutes of Health (Wyatt et al, Virology, (1995) 210:202-5).

Nucleic acid isolation: Viral RNA was isolated from the allantoic fluid of NDV-infected chicken embryos and infected DF-1 cells using the TRIzol-LS reagent according to the manufacturer's instructions (ThermoFisher Scientific). MD viral DNA extraction from tracheal and ocular swab samples was performed using the MagaZorbH DNA mini-prep 96-well kit (Promega, Madison, Wis.) as described previously (Johnson et al, Avian Dis., (2010) 54:1251-9).

Construction of a recombinant LaSota (NDV) cDNA clone containing the gB gene of MDV: A previously generated pLS-GFP infectious clone (Hu et al, supra; Zhao et al, supra) was used as a backbone to construct a recombinant LaSota cDNA clone with the MDV gB gene inserted between the phosphoprotein (P) and matrix (M) genes as an additional transcription unit. Briefly, the gB gene of MDV Strain AC722 (Dunn et al, J. Gen. Virol., (2019) 100:1132-39) (Dunn et al., 2019) (14) (Dunn, Black Pyrkosz et al. 2019) [14] [7] was optimized for codon usage based on codon frequencies in Gallus gallus and synthesized by GenScript (Piscataway, N.J., USA). The open reading frame (ORF) of the gB gene and the pLS-GFP vector were amplified by PCR with pfuUltra™ II Fusion HS DNA polymerase (Agilent Technologies, La Jolla, Calif., USA) utilizing gB- and vector-specific primers according to the manufacturer's instructions. Subsequently, the amplified gB ORF was cloned into the pLS-GFP vector to replace the GFP gene using the In-Fusion® PCR cloning kit following the manufacturer's instructions (Clontech, Mountain View, Calif., USA). The resulting recombinant, designated as pLS/MDV-gB (SEQ ID NO: 3), was propagated in Stbl2 cells at 30° C. for 24 hours and purified using a QIAprep Spin Miniprep kit (Qiagen, Valencia, Calif., USA).

Virus rescue and propagation: Rescue of the recombinant virus was performed by transfection of the full-length cDNA clone, pLS/MDV-gB, and supporting plasmids that express the NDV NP, P and L proteins into MVA/T7-infected HEp-2 cells as described previously (Estevez et al, Virus Res., (2007) 129:182-90). The rescued virus was amplified by inoculating 100 µl of the infected cell lysate into the allantoic cavity of 9-day-old SPF chicken embryos and incubating the embryos at 37° C. After 4 days of incubation, the AF was harvested, and the presence of the rescued virus was detected by hemagglutination (HA) assay (Alexander, D., "Newcastle Disease Virus and Other Avian Paramyxoviruses", p. 156-163, in Swayne D, Glisson J R, Jackwood M W, Pearson J E, Reed W M (ed), A laboratory manual for the isolation and identification of avian pathogens, 4th Edition ed. American Association of Avian Pathologists, Kennett Square, Pa.). HA-positive AF was filtered through a 0.22 µm Nalgene Syringe Filter (ThermoFisher Scientific), then diluted in PBS and amplified in chicken embryos three times. The AF was harvested from the infected embryos, aliquoted, and stored at −80° C. as a stock. The nucleotide sequence of the rescued virus was determined by sequencing the RT-PCR products amplified from the viral genome, as described previously (Hu et al, supra).

Figure 1:
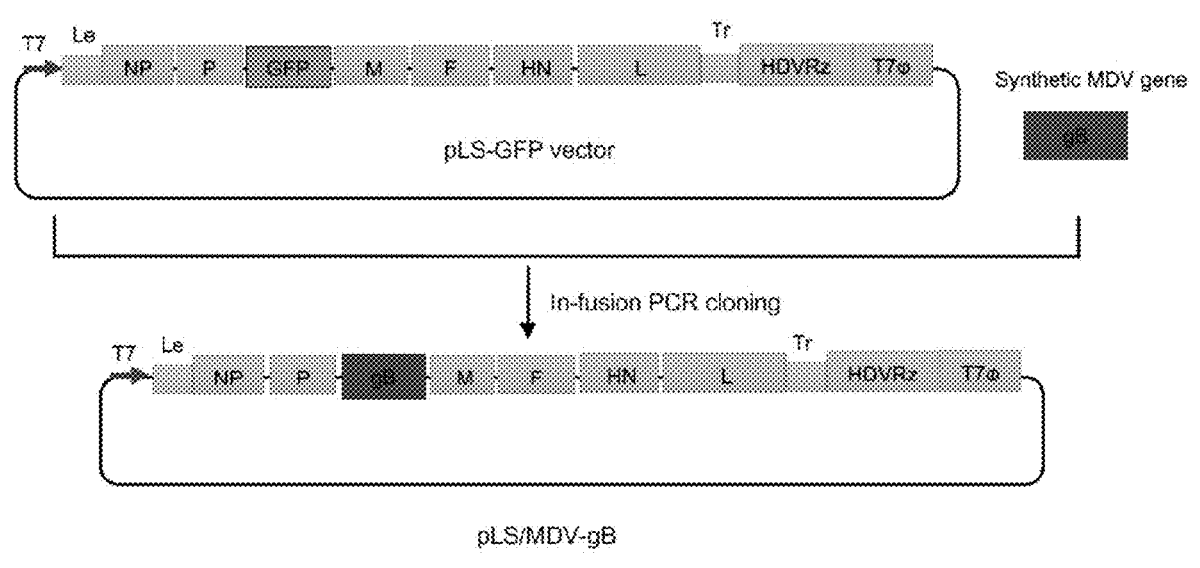

A full-length cDNA clone encoding the complete antisense genome of the NDV LaSota vaccine strain with the MDV gB gene was constructed using PCR and IN-FUSION PCR cloning (FIG. 1). The insertion of the transcription "cassettes" containing NDV trans-acting elements and the MDV gB gene ORF, increased the length of the recombinant clone by 2,796 bps. Thus, the total length of cDNA clone in the pLS/MDV-gB plasmids is 17,982 bps (SEQ ID NO: 3) and is divisible by 6 abiding by the "Rule of Six" (Kolakofsky et al, J. Gen. Virol., (2005) 86:1869-77). After co-transfection of the full-length cDNA clone and supporting plasmids into HEp-2 cells and subsequent propagation in SPF chicken embryonated eggs, the LaSota strain-based recombinant virus vectoring the MDV gB gene was successfully generated. The nucleotide sequence of the rescued recombinant virus, designated rLS/MDV-gB, was confirmed by sequencing analysis of the RT-PCR products of the viral genome (Data not shown).

Example 2

Biological Characterization of Recombinant rLS/MDV-gB Virus.

Titration, pathogenicity and growth dynamics analyses: Titers of rLS/MDV-gB and its parental rLaSota and rLS/GFP viruses were analyzed and compared using two methods: 1) a standard HA test in a 96-well microplate, and; 2) a 50% egg infective dose ($EID_{50}$) assay in 9-day-old SPF chicken embryos (Alexander, D., supra). Pathogenicity of these recombinant viruses was determined using the standard mean death time (MDT) in chicken embryos and intracerebral pathogenicity index (ICPI) assays in one-day-old SPF chickens (Alexander, D., supra). The growth kinetics of the recombinant virus in vitro was determined using DF-1 cells. DF-1 cells were infected with the rLS/MDV-gB virus at a multiplicity of infection (MOI) of 0.01. Every 12 h post-infection, the infected DF-1 cells were harvested by freezing and thawing two times and stored at −80° C. until tested. Viral titers were determined by the 50% tissue culture infective dose ($TCID_{50}$) assay on DF-1 cells for each time point in triplicates (Alexander, D., supra). The mean titer of each time point of the viruses is expressed in $Log_{10}$ $TCID_{50}$/mL. The parental rLaSota, and rLS/GFP viruses were included in the growth kinetic assay as controls.

MDT and ICPI tests were performed to determine whether the insertion of the MDV gB gene into the NDV LaSota genome affected the biological properties (i.e., pathogenicity and growth kinetics) of the recombinant rLS/

Figure 2:
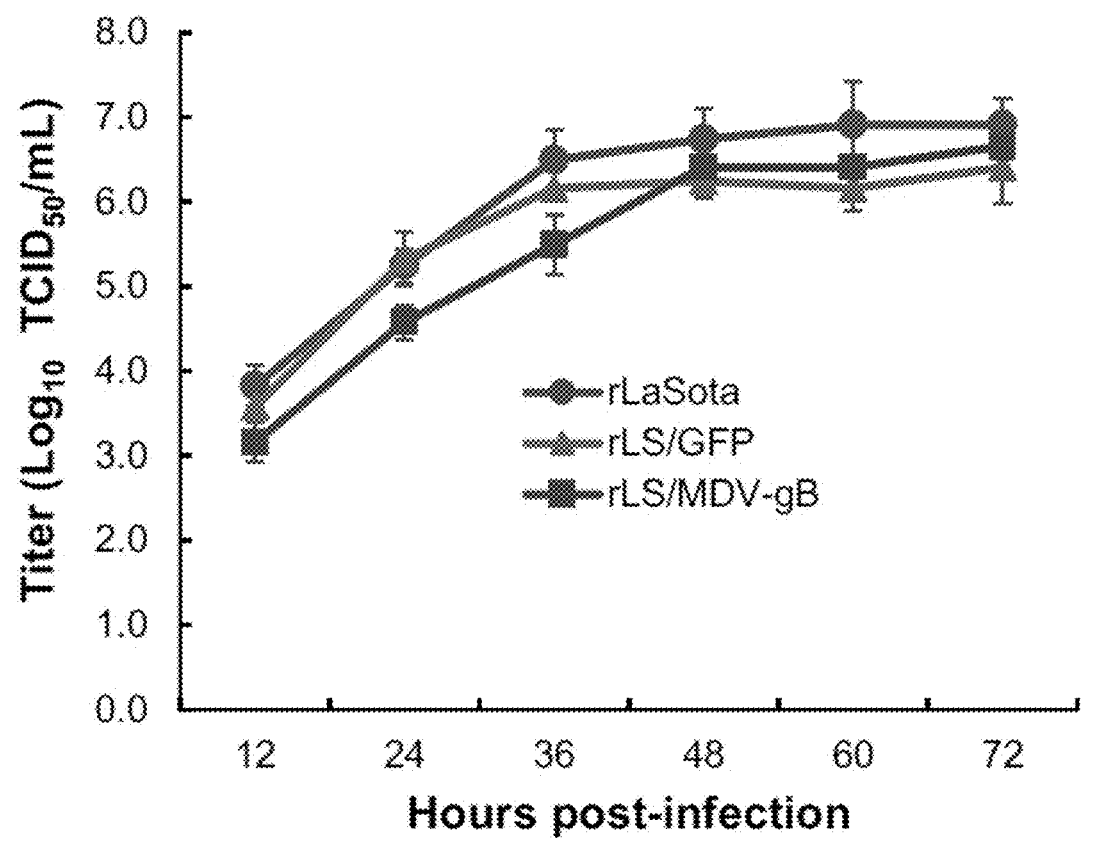

MDV-gB virus. As shown in Table 1, the recombinant virus was slightly attenuated with a lower ICPI (0.0) and higher MDT (>150 hs) than the parental rLaSota virus. The titer of the recombinant virus grown in embryonated eggs was comparable to the titers of the parental rLaSota and rLS/GFP viruses with a slightly lower HA titer (Table 1). Replication of the rLS/MDV-gB virus was initially delayed in the early stages (first 36 hours) of infection, but after time, it was able to replicate to similar titers compared to the parental rLaSota and rLS/GFP viruses (FIG. 2).

TABLE 1

Biological assessments of the recombinant viruses

| Viruses | MDT | ICPI | HA | $EID_{50}$ |
|---|---|---|---|---|
| rLaSota | 110 hs | 0.15 | $2^{11}$ | $2.37 \times 10^9$ |
| rLS/GFP | 140 hs | 0.0 | $2^{11}$ | $3.16 \times 10^9$ |
| rLS/MDV-gB | >150 hs | 0.0 | $2^8$ | $6.81 \times 10^9$ |

Expression of the MDV gB and NDV hemagglutinin (HN) proteins in cells infected with the recombinant rLS/MDV-gB virus: Expression of the MDV gB and NDV HN proteins in DF-1 cells infected with the rLS/MDV-gB virus was examined by immunofluorescence assay (IFA) with a polyclonal anti-MDV chicken serum (Md11) and an NDV-specific monoclonal antibody against the HN protein (Mab, a gift of Dr. Ron Iorio from University of Massachusetts Medical School, USA). Briefly, confluent monolayers of DF-1 cells were infected with rLaSota and rLS/MDV-gB viruses, respectively, at 0.01 MOI. After 24 hours the infected cells and control cells were washed with phosphate-buffered saline (PBS) and fixed with 10% zinc formalin (Fisher Scientific, Pittsburgh, Pa., USA) for 15 min at room temperature, followed by the addition of 0.5% Triton X-100 (Sigma, St. Louis, Mo.) for 10 min to permeabilize the cells at room temperature. The permeabilized cells were blocked with 5% goat serum (SouthernBiotech, Birmingham, Ala., USA) for 30 min at 37° C. After blocking, the cells were incubated for 1 hour with a mixture of anti-MDV sera (1:100 dilution) and mouse anti-NDV HN Mab (1:100 Dilution). Cells were washed with PBS and incubated with a mixture of FITC-labeled goat anti-chicken IgG (H+L) (SouthernBiotech, 1:1000 dilution) and ALEXA FLUOR 568 conjugated goat anti-mouse IgG (ThermoFisher Scientific, 1:1000 dilution) for 1 hour at 37° C. Finally, the infected cells were stained with DAPI (300 nM, ThermoFisher Scientific) for 5 min at room temperature. Cytopathic effect (CPE) and fluorescence images were monitored and photographed using an EVOS FL Cell Imaging System at 400× magnifications (ThermoFisher Scientific). Green, red, and blue fluorescence images that were photographed from the same field of virus-infected cells were merged into single images, respectively, to examine the co-localization of the MDV gB and NDV HN proteins.

Expression of the MDV gB and NDV HN proteins in the recombinant virus-infected DF-1 cells was examined by IFA. As shown in FIG. 3, red fluorescence (presenting NDV HN protein) was observed in rLaSota infected cells, but no green fluorescence (presenting MDV gB protein) was detected in the same field of infected cells, demonstrating the specificity of the antibodies and conjugates. When examining rLS/MDV-gB infected DF-1 cells, both green and red fluorescence was observed by fluorescence microscopy, indicative of gB and HN staining, respectively. After merging fluorescent images that were taken in the same field, green and red fluorescence co-localized to the same infected cells. These results confirm that the MDV gB protein was co-expressed with the NDV HN protein from the rLS/MDV-gB recombinant-infected cells.

Example 3

Vaccination Studies

Three animal experiments were performed to evaluate the protective efficacy of rLS/MDV-gB vaccine against MDV and NDV challenges. In experiments 1 and 2, Line $15I_5 \times 7_1$ white leghorn chickens ($F_1$ hybrid progeny of susceptible line $15I_5$ males and line $7_1$ females) were used in ABSL-2 facilities in ADOL to evaluate protection against MDV challenge. The breeding flock was routinely monitored for antibodies against MDV, avian leukosis virus, and reticuloendotheliosis virus and was negative for these viruses during the period of these experiments. Animal usage protocols for experiments 1 and 2 were approved by the Avian Disease and Oncology Laboratory Institutional Animal Care and Use Committee. In Experiment 3, SPF Leghorn chickens were used in the BSL-3E animal facilities at SEPRL to evaluate the protection against lethal NDV challenge. All chickens were housed in Horsfall isolators (Federal Designs, Inc., Comer, Ga.) with ad libitum access to feed and water. At the termination of the experiments, all birds were humanely euthanized following SEPRL's Institutional Animal Care and Use Committee (IACUC) approved animal use protocols.

Experiment 1: For measuring protection against MDV challenge in each of two replicates, birds were divided into four groups of 19 birds and vaccinated at hatch with 100 µl of PBS [Group 1], rLS-GFP [Group 2], or rLS/MDV-gB [Group 3] at a dose of $1.0 \times 10^6$ $EID_{50}$/bird via intranasal and intraocular (IN/IO) routes. All birds were challenged with virulent MDV (JM/102W) at a dose of 500 PFU/bird by intraperitoneal injection at 14 days post-vaccination (DPV). Birds were monitored daily and up to 8 weeks of age. On day 14 immediately before the challenge, birds were bled for determining antibody responses to the vaccines. All birds were necropsied and measured for MD percentage at termination and percent protection was calculated as: % Protection=(% MD in unvaccinated control−% MD in vaccinated group)/% MD in unvaccinated group)×10. Chi-square analysis was used to analyze differences in % MD between unvaccinated and vaccinated groups, with Fisher's exact test used when expected values were less than 5 in any group. Significant results were based on p-value<0.05. Data were analyzed with the statistical program JMP 14 (SAS Institute Inc., Cary, N.C., USA).

Experiment 2: For measuring the protection of chickens against an MDV challenge at an earlier age, methods from Expt.1 were repeated in each of the two replicates, except each group was challenged with virulent MDV (JM/102W, 500 PFU) at 5 DPV. Birds were monitored daily and up to 8 weeks of age. All birds were necropsied and measured for MD percentage, as described in Experiment 1.

Experiment 3: Thirty (30) one-day-old SPF Leghorn chickens were randomly divided into three groups of 10 birds. Birds were inoculated with 100 µl of PBS [Group 1], vaccinated with the rLS/GFP [Group 2], or rLS/MDV-gB [Group 3] at a dose of $1.0 \times 10^6$ $EID_{50}$/bird via IN/IO routes. At 14 DPV, the birds were challenged with a lethal dose of the NDV/CA02 virus, as described previously (Kapczynski & King, Vaccine, (2005) 23:3424-33). Serum samples were collected immediately before the challenge for NDV antibody detection using the standard HI assay (Alexander, D., supra). After the challenge, the birds were monitored daily for clinical signs of Newcastle disease and mortality for two weeks.)

In Experiment 1, birds vaccinated with the rLS/MDV-gB recombinant virus (SEQ ID NO: 3) developed a comparable level of HI antibody responses against NDV vector as its parental rLS/GFP virus at 14 DPV (Table 2) in both replicates. Birds were challenged at 14 DPV with virulent MDV and percentage (%) of Marek's disease was determined at necropsy at 8 weeks of age. Hemagglutination inhibition (HI) titer was expressed as $log_2$ of the mean±standard deviation.

TABLE 2

Serum antibody responses of chickens following vaccination in Experiment 1

| Treatment | Antibody response HI titer | |
|---|---|---|
| | Rep. 1 | Rep. 2 |
| PBS | 0.00 ± 0.00 | 0.00 ± 0.00 |
| rLS/GFP | 5.25 ± 1.71 | 5.42 ± 1.31 |
| rLS/MDV-gB | 4.78 ± 1.23 | 4.74 ± 1.05 |

As shown in Table 3, about 84-95% of birds in the PBS group and 100% of birds in the NDV vector control group (rLS/GFP) of both replicas developed typical MD pathological changes with either enlarged peripheral nerves or visceral tumors. In contrast, only 5% (Replicate 2) and 11% (Replicate 1) of birds in the rLS/MDV-gB vaccination group showed MD lesions, representing 89% and 95% protection in replicates 1 and 2, respectively, against virulent MDV challenge. Statistical analysis revealed that vaccination of SPF chickens with the rLS/MDV-gB virus conferred significant protection against MDV challenge when compared to unvaccinated PBS control (p<0.000/). In contrast, there were no significant differences between the unvaccinated and parental rLS/GFP virus (without MDV gene insertion) groups.

In Experiment 2, vaccinated SPF chickens were challenged at 5 DPV to examine if the rLS/MDV-gB recombinant provides protection of chickens against MD at an earlier age. At 5 DPV, all vaccinated birds had not developed a detectable level of serum HI antibody against the NDV vector yet. In the rLS/MDV-gB vaccination group, 27-33% of chickens were MD positive, whereas, in the control groups (PBS and rLS/GFP), 93-100% of birds developed MDV induced pathological changes (Table 3). The 77-83% protection against MD obtained in the rLS/MDV-gB vaccinated birds were significantly higher than that from the NDV vector control group (rLS/GFP). The result demonstrated that the rLS/MDV-gB vaccine could provide significant partial protection against MD in SPF birds as early as 5 DPV.

Immune response and protection against velogenic NDV challenge. To determine whether the MDV gB gene insertion affects the protective efficacy of NDV vectored vaccine against ND, the vaccinated SPF chickens were challenged with vNDV at 14 DPV. As shown in Table 4, all of the birds immunized with rLS/MDV-gB induced NDV-specific humoral immunity with a comparable HI antibody titer as the parental rLaSota vaccine. All birds in the unvaccinated control group (inoculated with PBS) displayed disease signs with conjunctivitis and severe depression from 2 to 3 days post-challenge (DPC) and 100% mortality at 4 DPC. In contrast, all chickens immunized with the rLaSota vaccine or the rLS/MDV-gB virus were completely protected against the NDV challenge without showing any signs of disease. The result obtained from this study demonstrated that the MDV gB gene insertion into the NDV vector did not alter the protective efficacy of the NDV vectored vaccine against ND. For the data in Table 4, HI titer is expressed as $log_2$ of the mean±standard deviation. Serum NDV HI titer equal or larger than 3 $log_2$ is deemed as positive.

TABLE 4

Serum antibody responses of chickens following vaccination and survivors after NDV challenge

| | Antibody responses | | | |
|---|---|---|---|---|
| Treatment | Seropositive birds | NDV HI titer | Disease signs | Survivors |
| PBS | 0/10 | 0 | 10/10 | 0/10 |
| rLaSota | 10/10 | 5.4 ± 1.3 | 0/10 | 10/10 |
| rLS/MDV-gB | 10/10 | 4.7 ± 1.0 | 0/10 | 10/10 |

TABLE 3

Clinical protection against MDV challenge

| | Experiment 1 | | Experiment 2 | |
|---|---|---|---|---|
| Treatment | % MD Pos (Rep1) | % MD Pos (Rep 2) | % MD Pos (Rep 1) | % MD Pos (Rep 2) |
| PBS | 95% | 84% | 93% | 100% |
| rLS/GFP | 100% (p = 1.00) | 100% (p = 0.2297) | 100% | 93% |
| rLS/MDV-gB | 11% (p < 0.0001) | 5% (p < 0.0001) | 27% (p < 0.01) | 33% (p < 0.01) |

While the invention has been described with reference to details of the illustrated embodiments, these details are not intended to limit the scope of the invention as defined in the appended claims. The embodiments of the invention in which exclusive property or privilege is claimed is defined as follows:

What is claimed is:

1. A composition comprising a nucleic acid at least 95% identical to SEQ ID NO:3.

2. The composition of claim 1, comprising a nucleic acid at least 99% identical to SEQ ID NO:3.

3. A vector comprising the nucleic acid of claim 1.

4. The vector of claim 3, wherein the vector comprises a nucleic acid encoding a synthetic polypeptide having an amino acid sequence at least 95% identical to SEQ ID NO:2.

5. The vector of claim 3, wherein the vector comprises a nucleic acid encoding a synthetic polypeptide comprising SEQ ID NO:2.

6. The vector of claim 3, wherein the recombinant NDV comprises a nucleic acid having at least 99% identity to SEQ ID NO:3.

7. The vector of claim 3, wherein the recombinant NDV comprises SEQ ID NO: 3.

8. A method of eliciting an immune response against Marek's disease virus (MDV) and Newcastle disease virus (NDV) in a subject, comprising administering to the subject a composition comprising a recombinant NDV, wherein the recombinant NDV comprises a nucleic acid having at least 95% identity to SEQ ID NO: 3.

9. The method of claim 8, wherein the recombinant NDV comprises a nucleic acid encoding a synthetic polypeptide having an amino acid sequence at least 95% identical to SEQ ID NO: 2.

10. The method of claim 8, wherein the recombinant NDV comprises a nucleic acid encoding a synthetic polypeptide comprising SEQ ID NO: 2.

11. The method of claim 8, wherein the recombinant NDV comprises a nucleic acid having at least 99% identity to SEQ ID NO: 3.

12. The method of claim 8, wherein the recombinant NDV comprises SEQ ID NO: 3.

13. The method of claim 8, wherein the subject is poultry.

14. The method of claim 9, wherein the subject is a chicken.

* * * * *

```
                              SEQUENCE LISTING

<160> NUMBER OF SEQ ID NOS: 3

<210> SEQ ID NO 1
<211> LENGTH: 2598
<212> TYPE: DNA
<213> ORGANISM: Artificial Sequence
<220> FEATURE:
<223> OTHER INFORMATION: Chemically Synthesized

<400> SEQUENCE: 1
atgcactact tcagaaggaa ctgcatcttc tttctgattg tgatcctgta cgggacaaac      60
agctcccctt ccacacagaa tgtgactagc cgcgaggtgt gagctccgt gcagctgtcc     120 gaggaagaga gcaccttta cctgtgcccc cctccagtgg gctccacagt gatcagactg     180
gaacccccta ggaagtgccc tgagccaaga aaagctactg aatggggga gggcattgca     240 atcctgttca aggagaacat tagcccatac aagtttaaag tgaccctgta ctacaaaaat     300
atcattcaga ccaaacttg gaccgggacc acatacaggc agatcacaaa ccgctacact     360
gaccggaccc ccgtgagcat tgaagagatc acagatctga ttgacggaaa ggggcggtgc     420
agctccaaag ctcgctacct gcggaacaac gtgtacgtgg aagcattcga tagagacgcc     480
ggagagaagc aggtgctgct gaagccatcc aagttcaaca cccccgaaag cagagcatgg     540
cacactacca atgagacata caccgtgtgg gggtcccccct ggatctacag gaccggcaca     600
agcgtgaact gcattgtgga agagatggac gcccgctccg tgttcccta cagctacttt     660 gccatggcta acggcgatat tgctaatatc tccccattct acggactgag cccaccagaa     720
gcagctgcag agccaatggg ctaccctcag gacaacttca agcagctgga tagctacttt     780
tccatggatc tggacaagcg ccggaaagct tccctgcccg tgaagaggaa tttcctgatc     840
accagccact ttacagtggg ctgggactgg gcacctaaaa caactcgcgt gtgcagcatg     900
acaaagtgga agaagtgac tgagatgctg agggccaccg tgaacggaag atacaggttc     960
atggctcgcg aactgtccgc aacattcatc agcaacacca cagagtttga ccctaatcgg    1020
atcattctgg acagtgcat taagagagaa gcagaggccg ctattgagca gatctttagg    1080
actaagtaca acgatagcca cgtgaaagtg gggcacgtgc agtacttcct ggccctgggc    1140
ggcttcatcg tggcttacca gccagtgctg agcaagtccc tggcccacat gtacctgcgg    1200
gaactgatga gagataacag gaccgacgag atgctggatc tggtgaacaa caagcacgcc    1260
atctacaaga aaatgctac aagcctgtcc aggctgagaa gggatattcg caacgctccc    1320
aatcggaaga tcacactgga tgacactacc gccatcaagt ccactagctc cgtgcagttc    1380
gccatgctgc agtttctgta cgaccacatt cagactcaca tcaacgatat gttcagcagg    1440
atcgcaaccg cctggtgcga actgcagaac cgcgagctgt gctgtggca cgagggcatt    1500 aagatcaatc cctccgctac tgcaagcgcc accctgggac gccgggtggc agcaaaaatg    1560 ctggggacg tggctgcagt gagctcctgc actgcaatcg atgccgagtc cgtgaccctg    1620
cagaacagca tgagagtgat cacttccacc aatacatgct acagcagacc tctggtgctg    1680
tttagctacg gggagaacca gggcaatatc cagggacagc tgggggaaaa caatgagctg    1740
ctgccaacac tggaagcagt ggagcccctgc tccgccaacc acagaaggta cttcctgttt    1800
ggcagcggat acgcactgtt cgaaaactac aattttgtga agatggtgga tgccgctgac    1860
```

-continued

```
attcagatcg cctccacatt cgtggagctg aatctgactc tgctggaaga tcgggagatc    1920
ctgccactga gcgtgtacac caaagaagag ctgagagacg tgggagtgct ggattacgct    1980
gaagtggcac gccggaacca gctgcacgag ctgaagtttt acgacattaa caaagtgatc    2040
gaagtggata caaactacgc tttcatgaat gggctggcag agctgtttaa cggaatggga    2100
caagtgggac aggcaatcgg gaaggtggtg gtgggagcag caggagctat tgtgagcacc    2160
atctccgggg tgagcgcatt catgtccaat cccttggcg ctctggcaat tggactgatc    2220
attatcgccg gcctggtggc tgcattcctg gcttacagat acgtgaacaa gctgaaaagc    2280
aatcctatga aggccctgta cccaatgaca actgaagtgc tgaaagccca ggctacacgc    2340
gagctgcacg cgaagagtc cgatgacctg gaaagaacta gcatcgacga gaggaagctg    2400
gaagaggctc gcgaaatgat caagtacatg gcactggtga gcgccgaaga gaggcacgag    2460
aagaaactga gaaggaagcg ccggggaacc acagcagtgc tgtccgatca cctggccaag    2520
atgagaatca aaaacagcaa tcccaagtac gacaaactgc ctactaccta cagcgattcc    2580
gaggatgacg ccgtgtga                                                 2598
```

<210> SEQ ID NO 2
<211> LENGTH: 865
<212> TYPE: PRT
<213> ORGANISM: Artificial Sequence
<220> FEATURE:
<223> OTHER INFORMATION: Chemically Synthesized

<400> SEQUENCE: 2

```
Met His Tyr Phe Arg Arg Asn Cys Ile Phe Phe Leu Ile Val Ile Leu
1               5                   10                  15

Tyr Gly Thr Asn Ser Ser Pro Ser Thr Gln Asn Val Thr Ser Arg Glu
            20                  25                  30

Val Val Ser Ser Val Gln Leu Ser Glu Glu Glu Ser Thr Phe Tyr Leu
        35                  40                  45

Cys Pro Pro Pro Val Gly Ser Thr Val Ile Arg Leu Glu Pro Pro Arg
    50                  55                  60

Lys Cys Pro Glu Pro Arg Lys Ala Thr Glu Trp Gly Glu Gly Ile Ala
65                  70                  75                  80

Ile Leu Phe Lys Glu Asn Ile Ser Pro Tyr Lys Phe Lys Val Thr Leu
                85                  90                  95

Tyr Tyr Lys Asn Ile Ile Gln Thr Thr Thr Trp Thr Gly Thr Thr Tyr
            100                 105                 110

Arg Gln Ile Thr Asn Arg Tyr Thr Asp Arg Thr Pro Val Ser Ile Glu
        115                 120                 125

Glu Ile Thr Asp Leu Ile Asp Gly Lys Gly Arg Cys Ser Ser Lys Ala
    130                 135                 140

Arg Tyr Leu Arg Asn Asn Val Tyr Val Glu Ala Phe Asp Arg Asp Ala
145                 150                 155                 160

Gly Glu Lys Gln Val Leu Leu Lys Pro Ser Lys Phe Asn Thr Pro Glu
                165                 170                 175

Ser Arg Ala Trp His Thr Thr Asn Glu Thr Tyr Thr Val Trp Gly Ser
            180                 185                 190

Pro Trp Ile Tyr Arg Thr Gly Thr Ser Val Asn Cys Ile Val Glu Glu
        195                 200                 205

Met Asp Ala Arg Ser Val Phe Pro Tyr Ser Tyr Phe Ala Met Ala Asn
    210                 215                 220

Gly Asp Ile Ala Asn Ile Ser Pro Phe Tyr Gly Leu Ser Pro Pro Glu
```

```
            225                 230                 235                 240
        Ala Ala Ala Glu Pro Met Gly Tyr Pro Gln Asp Asn Phe Lys Gln Leu
                            245                 250                 255

Asp Ser Tyr Phe Ser Met Asp Leu Asp Lys Arg Arg Lys Ala Ser Leu
                            260                 265                 270

Pro Val Lys Arg Asn Phe Leu Ile Thr Ser His Phe Thr Val Gly Trp
                            275                 280                 285

Asp Trp Ala Pro Lys Thr Thr Arg Val Cys Ser Met Thr Lys Trp Lys
                            290                 295                 300

Glu Val Thr Glu Met Leu Arg Ala Thr Val Asn Gly Arg Tyr Arg Phe
        305                 310                 315                 320

Met Ala Arg Glu Leu Ser Ala Thr Phe Ile Ser Asn Thr Thr Glu Phe
                            325                 330                 335

Asp Pro Asn Arg Ile Ile Leu Gly Gln Cys Ile Lys Arg Glu Ala Glu
                            340                 345                 350

Ala Ala Ile Glu Gln Ile Phe Arg Thr Lys Tyr Asn Asp Ser His Val
                            355                 360                 365

Lys Val Gly His Val Gln Tyr Phe Leu Ala Leu Gly Gly Phe Ile Val
                            370                 375                 380

Ala Tyr Gln Pro Val Leu Ser Lys Ser Leu Ala His Met Tyr Leu Arg
        385                 390                 395                 400

Glu Leu Met Arg Asp Asn Arg Thr Asp Glu Met Leu Asp Leu Val Asn
                            405                 410                 415

Asn Lys His Ala Ile Tyr Lys Lys Asn Ala Thr Ser Leu Ser Arg Leu
                            420                 425                 430

Arg Arg Asp Ile Arg Asn Ala Pro Asn Arg Lys Ile Thr Leu Asp Asp
                            435                 440                 445

Thr Thr Ala Ile Lys Ser Thr Ser Ser Val Gln Phe Ala Met Leu Gln
                            450                 455                 460

Phe Leu Tyr Asp His Ile Gln Thr His Ile Asn Asp Met Phe Ser Arg
        465                 470                 475                 480

Ile Ala Thr Ala Trp Cys Glu Leu Gln Asn Arg Glu Leu Val Leu Trp
                            485                 490                 495

His Glu Gly Ile Lys Ile Asn Pro Ser Ala Thr Ala Ser Ala Thr Leu
                            500                 505                 510

Gly Arg Arg Val Ala Ala Lys Met Leu Gly Asp Val Ala Ala Val Ser
                            515                 520                 525

Ser Cys Thr Ala Ile Asp Ala Glu Ser Val Thr Leu Gln Asn Ser Met
                            530                 535                 540

Arg Val Ile Thr Ser Thr Asn Thr Cys Tyr Ser Arg Pro Leu Val Leu
        545                 550                 555                 560

Phe Ser Tyr Gly Glu Asn Gln Gly Asn Ile Gln Gly Gln Leu Gly Glu
                            565                 570                 575

Asn Asn Glu Leu Leu Pro Thr Leu Glu Ala Val Glu Pro Cys Ser Ala
                            580                 585                 590

Asn His Arg Arg Tyr Phe Leu Phe Gly Ser Gly Tyr Ala Leu Phe Glu
                            595                 600                 605

Asn Tyr Asn Phe Val Lys Met Val Asp Ala Ala Asp Ile Gln Ile Ala
                            610                 615                 620

Ser Thr Phe Val Glu Leu Asn Leu Thr Leu Leu Glu Asp Arg Glu Ile
        625                 630                 635                 640

Leu Pro Leu Ser Val Tyr Thr Lys Glu Glu Leu Arg Asp Val Gly Val
                            645                 650                 655
```

Leu Asp Tyr Ala Glu Val Ala Arg Arg Asn Gln Leu His Glu Leu Lys
                660                 665                 670

Phe Tyr Asp Ile Asn Lys Val Ile Glu Val Asp Thr Asn Tyr Ala Phe
            675                 680                 685

Met Asn Gly Leu Ala Glu Leu Phe Asn Gly Met Gly Gln Val Gly Gln
        690                 695                 700

Ala Ile Gly Lys Val Val Val Gly Ala Ala Gly Ala Ile Val Ser Thr
705                 710                 715                 720

Ile Ser Gly Val Ser Ala Phe Met Ser Asn Pro Phe Gly Ala Leu Ala
                725                 730                 735

Ile Gly Leu Ile Ile Ile Ala Gly Leu Val Ala Ala Phe Leu Ala Tyr
            740                 745                 750

Arg Tyr Val Asn Lys Leu Lys Ser Asn Pro Met Lys Ala Leu Tyr Pro
        755                 760                 765

Met Thr Thr Glu Val Leu Lys Ala Gln Ala Thr Arg Glu Leu His Gly
    770                 775                 780

Glu Glu Ser Asp Asp Leu Glu Arg Thr Ser Ile Asp Glu Arg Lys Leu
785                 790                 795                 800

Glu Glu Ala Arg Glu Met Ile Lys Tyr Met Ala Leu Val Ser Ala Glu
                805                 810                 815

Glu Arg His Glu Lys Lys Leu Arg Arg Lys Arg Gly Thr Thr Ala
            820                 825                 830

Val Leu Ser Asp His Leu Ala Lys Met Arg Ile Lys Asn Ser Asn Pro
        835                 840                 845

Lys Tyr Asp Lys Leu Pro Thr Thr Tyr Ser Asp Ser Glu Asp Asp Ala
    850                 855                 860

Val
865

<210> SEQ ID NO 3
<211> LENGTH: 17982
<212> TYPE: DNA
<213> ORGANISM: Artificial Sequence
<220> FEATURE:
<223> OTHER INFORMATION: Chemically Synthesized

<400> SEQUENCE: 3
accaaacaga gaatccgtga gtcgcgataa aaggcgaaag agcaattgaa gtcacacggg      60
tagaaggtgt gaatctcgag tgcgagcccg aagcacaaac tcgagaaagc cttctgccaa    120
catgtcttcc gtatttgatg agtacgaaca gctcctcgcg gctcagactc gccccaatgg    180
agctcatgga gggggagaaa aagggagtac cttaaaagta gacgtcccgg tattcactct    240
taacagtgat gacccagaag atagatggag ctttgtggta ttctgcctcc ggattgctgt    300
tagcgaagat gccaacaaac cactcaggca aggtgctctc atatctcttt tatgctccca    360
ctcacaggta atgaggaacc atgttgccct tgcagggaaa cagaatgaag ccacattggc    420
cgtgcttgag attgatggct ttgccaacgg cacgccccag ttcaacaata ggagtggagt    480
gtctgaagag agagcacaga gatttgcgat gatagcagga tctctccctc gggcatgcag    540
caacggaacc ccgttcgtca cagccggggc cgaagatgat gcaccagaag acatcaccga    600
taccctggag aggatcctct ctatccaggc tcaagtatgg gtcacagtag caaaagccat    660
gactgcgtat gagactgcag atgagtcgga aacaaggcga atcaataagt atatgcagca    720
aggcagggtc caaaagaaat acatcctcta ccccgtatgc aggagcacaa tccaactcac    780

```
gatcagacag tctcttgcag tccgcatctt tttggttagc gagctcaaga gaggccgcaa   840
cacggcaggt ggtacctcta cttattataa cctggtaggg gacgtagact catacatcag   900
gaataccggg cttactgcat tcttcttgac actcaagtac ggaatcaaca ccaagacatc   960
agcccttgca cttagtagcc tctcaggcga catccagaag atgaagcagc tcatgcgttt  1020
gtatcggatg aaaggagata atgcgccgta catgacatta cttggtgata gtgaccagat  1080
gagctttgcg cctgccgagt atgcacaact ttactccttt gccatgggta tggcatcagt  1140
cctagataaa ggtactggga ataccaatt tgccagggac tttatgagca catcattctg  1200
gagacttgga gtagagtacg ctcaggctca gggaagtagc attaacgagg atatggctgc  1260
cgagctaaag ctaaccccag cagcaaggag gggcctggca gctgctgccc aacgggtctc  1320
cgaggagacc agcagcatag acatgcctac tcaacaagtc ggagtcctca ctgggcttag  1380 cgagggggggg tcccaagctc tacaaggcgg atcgaataga tcgcaagggc aaccagaagc  1440
cggggatggg gagacccaat tcctggatct gatgagagcg gtagcaaata gcatgaggga  1500
ggcgccaaac tctgcacagg gcactcccca atcggggcct cccccaactc ctgggccatc  1560
ccaagataac gacaccgact gggggtattg atggacaaaa cccagcctgc ttccacaaaa  1620
acatcccaat gccctcaccc gtagtcgacc cctcgatttg cggctctata tgaccacacc  1680
ctcaaacaaa catcccccctc tttcctccct ccccctgctg tacaactccg cacgccctag  1740
ataccacagg cacaatgcgg ctcactaaca atcaaaacag agccgaggga attagaaaaa  1800
agtacgggta aagagggat attcagagat cagggcaagt ctcccgagtc tctgctctct  1860
cctctacctg atagaccagg acaaacatgg ccaccttttac agatgcagag atcgacgagc  1920
tatttgagac aagtggaact gtcattgaca acataattac agcccagggt aaaccagcag  1980
agactgttgg aaggagtgca atcccacaag gcaagaccaa ggtgctgagc gcagcatggg  2040
agaagcatgg gagcatccag ccaccggcca gtcaaggcaa ccccgatcga caggacagat  2100
ctgacaaaca accatccaca cccgggcaaa cgaccccgca tgacagcccg ccggccacat  2160
ccgccgacca gccccccacc caggccacag acgaagccgt cgacacacag ctcaggaccg  2220
gagcaagcaa ctctctgctg ttgatgcttg acaagctcag caataaatcg tccaatgcta  2280
aaaagggccc atggtcgagc ccccaagagg ggaatcacca acgtccgact caacagcagg  2340
ggagtcaacc cagtcgcgga aacagtcagg aaagaccgca gaaccaagtc aaggccgccc  2400
ctggaaacca gggcacagac gtgaacacag catatcatgg acaatgggag gagtcacaac  2460
tatcagctgg tgcaaccccct catgctctcc gatcaaggca gagccaagac aatacccttg  2520
tatctgcgga tcatgtccag ccacctgtag actttgtgca agcgatgatg tctatgatgg  2580
aggcgatatc acagagagta agtaaggtcg actatcagct agatcttgtc ttgaaacaga  2640
catcctccat ccctatgatg cggtccgaaa tccaacagct gaaaacatct gttgcagtca  2700
tggaagccaa cttgggaatg atgaagattc tggatcccgg ttgtgccaac atttcatctc  2760
tgagtgatct acgggcagtt gcccgatctc acccggtttt agtttcaggc cctggagacc  2820
cctctcccta tgtgacacaa ggaggcgaaa tggcacttaa taaactttcg caaccagtgc  2880
cacatccatc tgaattgatt aaacccgcca ctgcatgcgg gcctgatata ggagtggaaa  2940
aggacactgt ccgtgcattg atcatgtcac gcccaatgca cccgagttct tcagccaagc  3000
tcctaagcaa gttagatgca gccgggtcga tcgaggaaat caggaaaatc aagcgccttg  3060
ctctaaatgg ctaattacta ctgccacacg tagcgggtcc ctgtccactc ggcatcacac  3120
ggaatctgca ccgagttccc ccccgcagac ccaaggtcca actctccaag cggcaatcct  3180
```

```
ctctcgcttc ttcagcccca ctgaatgatc gcgtaaccgt aattaatcta gctacattaa    3240
ggattaagaa aaaatacggg tagaattgga gtgccccaat tgtgagttta gttgatagtt    3300
gtagccacca tgcactactt cagaaggaac tgcatcttct ttctgattgt gatcctgtac    3360
gggacaaaca gctcccttc cacacagaat gtgactagcc gcgaggtggt gagctccgtg    3420
cagctgtccg aggaagagag cacctttac ctgtgccccc ctccagtggg ctccacagtg    3480
atcagactgg aacccctag gaagtgccct gagccaagaa aagctactga atgggggag    3540 ggcattgcaa tcctgttcaa ggagaacatt agcccataca agtttaaagt gaccctgtac    3600
tacaaaaata tcattcagac cacaacttgg accgggacca catacaggca gatcacaaac    3660
cgctacactg accggacccc cgtgagcatt gaagagatca cagatctgat tgacggaaag    3720
gggcggtgca gctccaaagc tcgctacctg cggaacaacg tgtacgtgga agcattcgat    3780
agagacgccg agagaagca ggtgctgctg aagccatcca gttcaacac ccccgaaagc    3840 agagcatggc acactaccaa tgagacatac accgtgtggg ggtccccctg gatctacagg    3900
accggcacaa gcgtgaactg cattgtggaa gagatggacg cccgctccgt gttcccttac    3960
agctactttg ccatggctaa cggcgatatt gctaatatct ccccattcta cggactgagc    4020
ccaccagaag cagctgcaga gccaatgggc taccctcagg acaacttcaa gcagctggat    4080
agctactttt ccatggatct ggacaagcgc cggaaagctt ccctgcccgt gaagaggaat    4140
ttcctgatca ccagccactt tacagtgggc tgggactggg cacctaaaac aactcgcgtg    4200
tgcagcatga caaagtggaa agaagtgact gagatgctga gggccaccgt gaacggaaga    4260
tacaggttca tggctcgcga actgtccgca acattcatca gcaacaccac agagtttgac    4320
cctaatcgga tcattctggg acagtgcatt aagagagaag cagaggccgc tattgagcag    4380
atctttagga ctaagtacaa cgatagccac gtgaaagtgg ggcacgtgca gtacttcctg    4440
gccctgggcg gcttcatcgt ggcttaccag ccagtgctga gcaagtccct ggcccacatg    4500
tacctgcggg aactgatgag agataacagg accgacgaga tgctggatct ggtgaacaac    4560
aagcacgcca tctacaagaa aaatgctaca agcctgtcca ggctgagaag ggatattcgc    4620
aacgctccca atcggaagat cacactggat gacactaccg ccatcaagtc cactagctcc    4680
gtgcagttcg ccatgctgca gtttctgtac gaccacattc agactcacat caacgatatg    4740
ttcagcagga tcgcaaccgc ctggtgcgaa ctgcagaacc gcgagctggt gctgtggcac    4800
gagggcatta agatcaatcc ctccgctact gcaagcgcca ccctgggacg ccgggtggca    4860
gcaaaaatgc tggggggacgt ggctgcagtg agctcctgca ctgcaatcga tgccgagtcc    4920
gtgaccctgc agaacagcat gagagtgatc acttccacca atacatgcta cagcagacct    4980
ctggtgctgt ttagctacgg ggagaaccag ggcaatatcc agggacagct gggggaaaac    5040
aatgagctgc tgccaacact ggaagcagtg gagccctgct ccgccaacca cagaaggtac    5100
ttcctgtttg gcagcggata cgcactgttc gaaaactaca atttgtgaa gatggtggat    5160 gccgctgaca ttcagatcgc ctccacattc gtggagctga atctgactct gctggaagat    5220
cgggagatcc tgccactgag cgtgtacacc aaagaagagc tgagagacgt gggagtgctg    5280
gattacgctg aagtggcacg ccggaaccag ctgcacgagc tgaagttta cgacattaac    5340 aaagtgatcg aagtggatac aaactacgct tcatgaatg ggctggcaga gctgtttaac    5400
ggaatgggac aagtgggaca ggcaatcggg aaggtggtgg tgggagcagc aggagctatt    5460
gtgagcacca tctccggggt gagcgcattc atgtccaatc cctttggcgc tctggcaatt    5520
```

```
ggactgatca ttatcgccgg cctggtggct gcattcctgg cttacagata cgtgaacaag   5580
ctgaaaagca atcctatgaa ggccctgtac ccaatgacaa ctgaagtgct gaaagcccag   5640
gctacacgcg agctgcacgg cgaagagtcc gatgacctgg aaagaactag catcgacgag   5700
aggaagctgg aagaggctcg cgaaatgatc aagtacatgg cactggtgag cgccgaagag   5760
aggcacgaga agaaactgag aaggaagcgc cggggaacca cagcagtgct gtccgatcac   5820
ctggccaaga tgagaatcaa aaacagcaat cccaagtacg acaaactgcc tactacctac   5880
agcgattccg aggatgacgc cgtgtgagtg tgtaactacc gtgtactaag ccccactcac   5940
ccagatcatc atgacacaaa aaactaatcg ttacctctct cgcttcctca gccccactga   6000
atgatcgcgt aaccgtaatt aatctagcta cattaaggat taagaaaaaa tacgggtaga   6060
attggagtgc cccaattgtg ccaagatgga ctcatctagg acaattgggc tgtactttga   6120
ttctgcccat tcttctagca acctgttagc atttccgatc gtcctacaag acacaggaga   6180
tgggaagaag caaatcgccc cgcaatatag gatccagcgc cttgacttgt ggactgatag   6240
taaggaggac tcagtattca tcaccaccta tggattcatc tttcaagttg gaatgaagaa   6300
agccactgtc ggcatgatcg atgataaacc caagcgcgag ttactttccg ctgcgatgct   6360
ctgcctagga agcgtcccaa ataccggaga ccttattgag ctggcaaggg cctgtctcac   6420
tatgatagtc acatgcaaga agagtgcaac taatgctgag agaatggttt tctcagtagt   6480
gcaggcaccc caagtgctgc aaagctgtag ggttgtggca aacaaatact catcagtgaa   6540
tgcagtcaag cacgtgaaag cgccagagaa gattcccggg agtggaaccc tagaatacaa   6600
ggtgaacttt gtctccttga ctgtggtacc gaagaaggat gtctacaaga tccctgctgc   6660
agtattgaag gtttctggct cgagtctgta caatcttgcg ctcaatgtca ctattaatgt   6720
ggaggtagac ccgaggagtc ctttggttaa atctctgtct aagtctgaca gcggatacta   6780
tgctaacctc ttcttgcata ttggacttat gaccaccgta gataggaagg ggaagaaagt   6840
gacatttgac aagctggaaa agaaaataag gagccttgat ctatctgtcg ggctcagtga   6900
tgtgctcggg ccttccgtgt tggtaaaagc aagaggtgca cggactaagc ttttggcacc   6960
tttcttctct agcagtggga cagcctgcta tcccatagca aatgcttctc ctcaggtggc   7020
caagatactc tggagtcaaa ccgcgtgcct gcggagcgtt aaaatcatta tccaagcagg   7080
tacccaacgc gctgtcgcag tgaccgccga ccacgaggtt acctctacta agctggagaa   7140
ggggcacacc cttgccaaat acaatcctt t taagaaataa gctgcgtctc tgagattgcg   7200
ctccgcccac tcacccagat catcatgaca caaaaaacta atctgtcttg attatttaca   7260
gttagttaac ctgtctatca agttagaaaa aacacgggta gaagattctg gatcccggtt   7320
ggcgccctcc aggtgcaaga tgggctccag accttctacc aagaacccag cacctatgat   7380
gctgactatc cggggttgcgc tggtactgag ttgcatctgt ccggcaaact ccattgatgg   7440
caggcctctt gcagctgcag gaattgtggt tacaggagac aaagccgtca acatatacac   7500
ctcatcccag acaggatcaa tcatagttaa gctcctcccg aatctgccca aggataagga   7560
ggcatgtgcg aaagcccct tggatgcata caacaggaca ttgaccactt tgctcacccc   7620
ccttggtgac tctatccgta ggatacaaga gtctgtgact acatctggag gggggagaca   7680
ggggcgcctt ataggcgcca ttattggcgg tgtggctctt ggggttgcaa ctgccgcaca   7740
aataacagcg gccgcagctc tgatacaagc caaacaaaat gctgccaaca tcctccgact   7800
taaagagagc attgccgcaa ccaatgaggc tgtgcatgag gtcactgacg gattatcgca   7860
actagcagtg gcagttggga agatgcagca gtttgttaat gaccaactta ataaaacagc   7920
```

```
tcaggaatta gactgcatca aaattgcaca gcaagttggt gtagagctca acctgtacct    7980
aaccgaattg actacagtat tcggaccaca aatcacttca cctgctttaa acaagctgac    8040
tattcaggca ctttacaatc tagctggtgg aaatatggat tacttattga ctaagttagg    8100
tgtagggaac aatcaactca gctcattaat cggtagcggc ttaatcaccg gtaaccctat    8160
tctatacgac tcacagactc aactcttggg tatacgggta actctacctt cagtcgggaa    8220
cctaaataat atgcgtgcca cctacttgga aaccttatcc gtaagcacaa ccaggggatt    8280
tgcctcggca cttgtcccca aagtggtgac acaggtcggt tctgtgatag aagaacttga    8340
cacctcatac tgtatagaaa ctgacttaga tttatattgt acaagaatag taacgttccc    8400
tatgtcccct ggtatttatt cctgcttgag cggcaatacg tcggcctgta tgtactcaaa    8460
gaccgaaggc gcacttacta caccatacat gactatcaaa ggttcagtca tcgccaactg    8520
caagatgaca acatgtagat gtgtaaaccc cccgggtatc atatcgcaaa actatggaga    8580
agccgtgtct ctaatagata aacaatcatg caatgtttta tccttaggcg ggataacttt    8640
aaggctcagt ggggaattcg atgtaactta tcagaagaat atctcaatac aagattctca    8700
agtaataata acaggcaatc ttgatatctc aactgagctt gggaatgtca acaactcgat    8760
cagtaatgct ttgaataagt tagaggaaag caacagaaaa ctagacaaag tcaatgtcaa    8820
actgactagc acatctgctc tcattaccta tatcgttttg actatcatat ctcttgtttt    8880
tggtatactt agcctgattc tagcatgcta cctaatgtac aagcaaaagg cgcaacaaaa    8940
gaccttatta tggcttggga ataatactct agatcagatg agagccacta caaaaatgtg    9000
aacacagatg aggaacgaag gtttccctaa tagtaatttg tgtgaaagtt ctggtagtct    9060
gtcagttcag agagttaaga aaaaactacc ggttgtagat gaccaaagga cgatatacgg    9120
gtagaacggt aagagaggcc gcccctcaat tgcgagccag gcttcacaac ctccgttcta    9180
ccgcttcacc gacaacagtc ctcaatcatg gaccgcgccg ttagccaagt tgcgttagag    9240
aatgatgaaa gagaggcaaa aaatacatgg cgcttgatat tccggattgc aatcttattc    9300
ttaacagtag tgaccttggc tatatctgta gcctcccttt tatatagcat ggggctagc    9360 acacctagcg atcttgtagg cataccgact aggaattcca gggcagaaga aaagattaca    9420
tctacacttg gttccaatca agatgtagta gataggatat ataagcaagt ggcccttgag    9480
tctccgttgg cattgttaaa aactgagacc acaattatga acgcaataac atctctctct    9540
tatcagatta atggagctgc aaacaacagt gggtggggg cacttatcca tgacccagat    9600
tatatagggg ggataggcaa agaactcatt gtagatgatg ctagtgatgt cacatcattc    9660
tatccctctg catttcaaga acatctgaat tttatcccgg cgcctactac aggatcaggt    9720
tgcactcgaa taccctcatt tgacatgagt gctacccatt actgctacac ccataatgta    9780
atattgtctg gatgcagaga tcactcacat tcatatcagt atttagcact tggtgtgctc    9840
cggacatctg caacagggag ggtattcttt tctactctgc gttccatcaa cctgacgac    9900 acccaaaatc ggaagtcttg cagtgtgagt gcaactcccc tgggttgtga tatgctgtgc    9960
tcgaaagtca cggagacaga ggaagaagat tataactcag ctgtccctac gcggatggta    10020
catgggaggt tagggttcga cggccagtac cacgaaaagg acctagatgt cacaacatta    10080 ttcgggggact gggtggccaa ctacccagga gtaggggggtg gatcttttat tgacagccgc    10140
gtatggttct cagtctacgg aggggttaaaa cccaattcac ccagtgacac tgtacaggaa    10200
gggaaatatg tgatatacaa gcgatacaat gacacatgcc cagatgagca agactaccag    10260
```

```
attcgaatgg ccaggtcttc gtataagcct ggacggtttg gtgggaaacg catacagcag    10320
gctatcttat ctatcaaggt gtcaacatcc ttaggcgaag acccggtact gactgtaccg    10380
cccaacacag tcacactcat gggggccgaa ggcagaattc tcacagtagg gacatctcat    10440
ttcttgtatc aacgagggtc atcatacttc tctcccgcgt tattatatcc tatgacagtc    10500
agcaacaaaa cagccactct tcatagtcct tatacattca atgccttcac tcggccaggt    10560
agtatccctt gccaggcttc agcaagatgc cccaacccgt gtgttactgg agtctataca    10620
gatccacatc ccctaatctt ctatagaaac cacaccttgc gaggggtatt cgggacaatg    10680
cttgatggtg tacaagcaag acttaaccct gcgtctgcag tattcgatag cacatcccgc    10740
agtcgcatta ctcgagtgag ttcaagcagt accaaagcag catacacaac atcaacttgt    10800
tttaaagtgg tcaagactaa taagacctat tgtctcagca ttgctgaaat atctaatact    10860
ctcttcggag aattcagaat cgtcccgtta ctagttgaga tcctcaaaga tgacggggtt    10920
agagaagcca ggtctggcta gttgagtcaa ttataaagga gttggaaaga tggcattgta    10980
tcacctatct tctgcgacat caagaatcaa accgaatgcc ggcgcgtgct cgaattccat    11040
gttgccagtt gaccacaatc agccagtgct catgcgatca gattaagcct tgtcaatagt    11100
ctcttgatta agaaaaaatg taagtggcaa tgagatacaa ggcaaaacag ctcatggtaa    11160
ataatacggg tagaacatgg cgagctccgg tcctgaaagg gcagagcatc agattatcct    11220
accagagtca cacctgtctt caccattggt caagcacaaa ctactctatt actgaaaatt    11280
aactgggcta ccgcttcctg atgaatgtga cttcgaccac ctcattctca gccgacaatg    11340
gaaaaaaata cttgaatcgg cctctcctga tactgagaga atgatagaac tcggaagggc    11400
agtacaccaa actcttaacc acaattccag aataaccgga gtgctccacc ccaggtgttt    11460
agaagaactg gctaatattg aggtcccaga ttcaaccaac aaatttcgga agattgagaa    11520
gaagatccaa attcacaaca cgagatatgg agaactgttc acaaggctgt gtacgcatat    11580
agagaagaaa ctgctggggt catcttggtc taacaatgtc ccccggtcag aggagttcag    11640
cagcattcgt acggatccgg cattctggtt tcactcaaaa tggtccacag ccaagtttgc    11700
atggctccat ataaaacaga tccagaggca tctgatggtg gcagctagga caaggtctgc    11760
ggccaacaaa ttggtgatgc taacccataa ggtaggccaa gtctttgtca ctcctgaact    11820
tgtcgttgtg acgcatacga atgagaacaa gttcacatgt cttacccagg aacttgtatt    11880
gatgtatgca gatatgatgg agggcagaga tatggtcaac ataatatcaa ccacggcggt    11940
gcatctcaga agcttatcag agaaaattga tgacattttg cggttaatag acgctctggc    12000
aaaagacttg ggtaatcaag tctacgatgt tgtatcacta atggagggat ttgcatacgg    12060
agctgtccag ctactcgagc cgtcaggtac atttgcagga gatttcttcg cattcaacct    12120
gcaggagctt aaagacattc taattggcct cctccccaat gatatagcag aatccgtgac    12180
tcatgcaatc gctactgtat tctctggttt agaacagaat caagcagctg agatgttgtg    12240
tctgttgcgt ctgtggggtc acccactgct tgagtcccgt attgcagcaa aggcagtcag    12300
gagccaaatg tgcgcaccga aaatggtaga ctttgatatg atccttcagg tactgtcttt    12360
cttcaaggga acaatcatca acgggtacag aaagaagaat gcaggtgtgt ggccgcgagt    12420
caaagtggat acaatatatg ggaaggtcat tgggcaacta catgcagatt cagcagagat    12480
ttcacacgat atcatgttga gagagtataa gagtttatct gcacttgaat ttgagccatg    12540
tatagaatat gaccctgtca ccaacctgag catgttccta aaagacaagg caatcgcaca    12600
ccccaacgat aattggcttg cctcgtttag gcggaacctt ctctccgaag accagaagaa    12660
```

```
acatgtaaaa gaagcaactt cgactaatcg cctcttgata gagttttttag agtcaaatga    12720 ttttgatcca tataaagaga tggaatatct gacgacccct tgagtaccta gagatgcaaa    12780
tgtggcagta tcatactcgc tcaaggagaa ggaagtgaaa gttaatggac ggatcttcgc    12840
taagctgaca aagaagttaa ggaactgtca ggtgatggcg gaagggatcc tagccgatca    12900
gattgcacct ttctttcagg gaaatggagt cattcaggat agcatatcct tgaccaagag    12960
tatgctagcg atgagtcaac tgtctttttaa cagcaataag aaacgtatca ctgactgtaa    13020
agaaagagta tcttcaaacc gcaatcatga tccgaaaagc aagaaccgtc ggagagttgc    13080
aaccttcata acaactgacc tgcaaaagta ctgtcttaat tggagatatc agacgatcaa    13140
attgttcgct catgccatca atcagttgat gggcctacct catttcttcg agtggattca    13200
cctaagactg atggacacta cgatgttcgt aggagaccct ttcaatcctc caagtgaccc    13260
tactgactgt gacctctcaa gagtccctaa tgatgacata tatattgtca gtgccagagg    13320
gggtatcgaa ggattatgcc agaagctatg gacaatgatc tcaattgctg caatccaact    13380
tgctgcagct agatcgcatt gtcgtgttgc ctgtatggta cagggtgata atcaagtaat    13440
agcagtaacg agagaggtaa gatcagatga ctctccggag atggtgttga cacagttgca    13500
tcaagccagt gataatttct tcaaggaatt aatccatgtc aatcatttga ttggccataa    13560
tttgaaggat cgtgaaacca tcaggtcaga cacattcttc atatacagca aacgaatctt    13620
caaagatgga gcaatcctca gtcaagtcct caaaaattca tctaaattag tgctagtgtc    13680
aggtgatctc agtgaaaaca ctgtaatgtc ctgtgccaac attgcctcta ctgtagcacg    13740
gctatgcgag aacgggcttc ccaaagactt ctgttactat ttaaactata taatgagttg    13800
tgtgcagaca tactttgact ctgagttctc catcaccaac aattcgcacc ccgatcttaa    13860
tcagtcgtgg attgaggaca tctcttttgt gcactcatat gttctgactc ctgcccaatt    13920 aggggggactg agtaaccttc aatactcaag gctctacact agaaatatcg gtgacccggg    13980
gactactgct tttgcagaga tcaagcgact agaagcagtg ggattactga gtcctaacat    14040
tatgactaat atcttaacta ggccgcctgg gaatggagat tgggccagtc tgtgcaacga    14100
cccatactct ttcaattttg agactgttgc aagcccaaat attgttctta agaaacatac    14160
gcaaagagtc ctatttgaaa cttgttcaaa tcccttattg tctggagtgc acacagagga    14220
taatgaggca gaagagaagg cattggctga attcttgctt aatcaagagg tgattcatcc    14280
ccgcgttgcg catgccatca tggaggcaag ctctgtaggt aggagaaagc aaattcaagg    14340
gcttgttgac acaacaaaca ccgtaattaa gattgcgctt actaggaggc cattaggcat    14400
caagaggctg atgcggatag tcaattattc tagcatgcat gcaatgctgt ttagagacga    14460 tgtttttttcc tccagtagat ccaaccaccc cttagtctct tctaatatgt gttctctgac    14520
actggcagac tatgcacgga atagaagctg gtcacctttg acgggaggca ggaaaatact    14580
gggtgtatct aatcctgata cgatagaact cgtagagggt gagattctta gtgtaagcgg    14640
agggtgtaca agatgtgaca gcggagatga acaatttact tggttccatc ttccaagcaa    14700
tatagaattg accgatgaca ccagcaagaa tcctccgatg agggtaccat atctcgggtc    14760
aaagacacag gagaggagag ctgcctcact tgcaaaaata gctcatatgt cgccacatgt    14820
aaaggctgcc ctaagggcat catccgtgtt gatctgggct tatgggata atgaagtaaa    14880 ttggactgct gctcttacga ttgcaaaatc tcggtgcaat gtaaacttag agtatcttcg    14940
gttactgtcc cctttacccca cggctgggaa tcttcaacat agactagatg atggtataac    15000
```

```
tcagatgaca ttcacccctg catctctcta cagggtgtca ccttacattc acatatccaa    15060
tgattctcaa aggctgttca ctgaagaagg agtcaaagag gggaatgtgg tttaccaaca    15120
gatcatgctc ttgggtttat ctctaatcga atcgatcttt ccaatgacaa caaccaggac    15180
atatgatgag atcacactgc acctacatag taaatttagt tgctgtatca gagaagcacc    15240
tgttgcggtt cctttcgagc tacttggggt ggtaccggaa ctgaggacag tgacctcaaa    15300
taagtttatg tatgatccta gccctgtatc ggagggagac tttgcgagac ttgacttagc    15360
tatcttcaag agttatgagc ttaatctgga gtcatatccc acgatagagc taatgaacat    15420
tctttcaata tccagcggga agttgattgg ccagtctgtg gtttcttatg atgaagatac    15480
ctccataaag aatgatgcca taatagtgta tgacaatacc cgaaattgga tcagtgaagc    15540
tcagaattca gatgtggtcc gcctatttga atatgcagca cttgaagtgc tcctcgactg    15600
ttcttaccaa ctctattacc tgagagtaag aggcctagac aatattgtct tatatatggg    15660
tgatttatac aagaatatgc caggaattct actttccaac attgcagcta caatatctca    15720
tcctgtcatt cattcaaggt tacatgcagt gggcctggtc aaccatgacg gatcacacca    15780
acttgcagat acggatttta tcgaaatgtc tgcaaaactg ttagtatctt gcacccgacg    15840
tgtgatctcc ggcttatatt caggaaataa gtatgatctg ctgttcccat ctgtcttaga    15900
tgataacctg aatgagaaga tgcttcagct gatatcccgg ttatgctgtc tgtacacggt    15960
actctttgct acaacaagag aaatcccgaa aataagaggc ttaactgcag aagagaaatg    16020
ttcaatactc actgagtatt tactgtcgga tgctgtgaaa ccattactta gccccgatca    16080
agtgagctct atcatgtctc ctaacataat tacattccca gctaatctgt actacatgtc    16140
tcggaagagc ctcaatttga tcagggaaag ggaggacagg gatactatcc tggcgttgtt    16200
gttcccccaa gagccattat tagagttccc ttctgtgcaa gatattggtg ctcgagtgaa    16260
agatccattc acccgacaac ctgcggcatt tttgcaagag ttagatttga gtgctccagc    16320
aaggtatgac gcattcacac ttagtcagat tcatcctgaa ctcacatctc caaatccgga    16380
ggaagactac ttagtacgat acttgttcag agggataggg actgcatctt cctcttggta    16440
taaggcatcc catctccttt ctgtacccga ggtaagatgt gcaagacacg gaactcctt    16500 atacttggct gaaggaagcg gagccatcat gagtcttctt gaactgcatg taccacatga    16560
aactatctat tacaatacgc tctttttcaaa tgagatgaac cccccgcaac gacatttcgg    16620 gccgaccccca actcagtttt tgaattcggt tgtttatagg aatctacagg cggaggtaac    16680
atgcaaggat ggatttgtcc aagagttccg tccattatgg agagaaaata cagaggaaag    16740
tgacctgacc tcagataaag cagtgggggta tattacatct gcagtaccct acagatctgt    16800
atcattgctg cattgtgaca ttgaaattcc tccagggtcc aatcaaagct tactagatca    16860
actagctatc aatttatctc tgattgccat gcattctgta agggagggcg gggtagtaat    16920
catcaaagtg ttgtatgcaa tgggatacta ctttcatcta ctcatgaact tgtttgctcc    16980
gtgttccaca aaaggatata ttctctctaa tggttatgca tgtcgagggg atatggagtg    17040
ttacctggta tttgtcatgg gttacctggg cgggcctaca tttgtacatg aggtggtgag    17100
gatggcaaaa actctggtgc agcggcacgg tacgcttttg tctaaatcag atgagatcac    17160
actgaccagg ttattcacct cacagcggca gcgtgtgaca gacatcctat ccagtccttt    17220
accaagatta ataaagtact tgaggaagaa tattgacact gcgctgattg aagccggggg    17280
acagcccgtc cgtccattct gtgcggagag tctggtgagc acgctagcga acataactca    17340
gataacccag atcatcgcta gccacattga cacagttatc cggtctgtga tatatatgga    17400
```

```
agctgagggt gatctcgctg acacagtatt tctatttacc ccttacaatc tctctactga  17460
cgggaaaaag aggacatcac ttaaacagtg cacgagacag atcctagagg ttacaatact  17520
aggtcttaga gtcgaaaatc tcaataaaat aggcgatata atcagcctag tgcttaaagg  17580
catgatctcc atggaggacc ttatcccact aaggacatac ttgaagcata gtacctgccc  17640
taaatatttg aaggctgtcc taggtattac caaactcaaa gaaatgttta cagacacttc  17700
tgtactgtac ttgactcgtg ctcaacaaaa attctacatg aaaactatag gcaatgcagt  17760
caaaggatat tacagtaact gtgactccta acgaaaatca catattaata ggctcctttt  17820
ttggccaatt gtattcttgt tgatttaatt atattatgtt agaaaaaagt tgaactctga  17880
ctccttagga ctcgaattcg aactcaaata aatgtcttta aaaaaggttg cgcacaatta  17940
ttcttgagtg tagtctcgtc attcaccaaa tctttgtttg gt                     17982
```